(12) United States Patent
Carson et al.

(10) Patent No.: US 6,610,661 B1
(45) Date of Patent: Aug. 26, 2003

(54) IMMUNOSTIMULATORY POLYNUCLEOTIDE/ IMMUNOMODULATORY MOLECULE CONJUGATES

(75) Inventors: Dennis A. Carson, Del Mar, CA (US); Eyal Raz, Del Mar, CA (US); Mark Roman, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/308,036

(22) PCT Filed: Oct. 9, 1997

(86) PCT No.: PCT/US97/19004

§ 371 (c)(1),
(2), (4) Date: Feb. 16, 2000

(87) PCT Pub. No.: WO98/16247

PCT Pub. Date: Apr. 23, 1998

Related U.S. Application Data
(60) Provisional application No. 60/028,118, filed on Oct. 11, 1996.

(51) Int. Cl.[7] .................. A61K 31/70; A61K 39/385; A61K 35/00; C07H 21/04

(52) U.S. Cl. .................. 514/44; 424/193.1; 424/185.1; 424/184.1; 536/23.1

(58) Field of Search .................. 514/44; 536/23.1, 536/24.1; 435/320.1, 375; 424/184.1, 185.1, 193.1

(56) References Cited

U.S. PATENT DOCUMENTS

| | | | |
|---|---|---|---|
| 1,234,718 A | 9/1917 | Hilleman et al. | 514/44 |
| 3,725,545 A | 4/1973 | Maes | 514/44 |
| 3,906,092 A | 9/1975 | Hilleman et al. | 424/209.1 |
| 4,849,513 A | 7/1989 | Smith et al. | 536/26.6 |
| 5,015,733 A | 5/1991 | Smith et al. | 536/23 |
| 5,118,800 A | 6/1992 | Smith et al. | 536/23 |
| 5,118,802 A | 6/1992 | Smith et al. | 536/27 |
| 5,268,365 A | 12/1993 | Rudolph et al. | 514/44 |
| 5,276,019 A | 1/1994 | Cohen et al. | 514/44 |
| 5,278,302 A | 1/1994 | Caruthers et al. | 536/24.5 |
| 5,453,496 A | 9/1995 | Caruthers et al. | 536/24.5 |
| 5,580,859 A | 12/1996 | Felgner et al. | 514/44 |
| 5,589,466 A | 12/1996 | Felgner et al. | 514/44 |
| 5,663,153 A | 9/1997 | Hutcherson et al. | 514/44 |
| 5,703,055 A | 12/1997 | Felgner et al. | 514/44 |
| 5,780,448 A * | 7/1998 | Davis | 514/44 |
| 6,037,329 A * | 3/2000 | Baird et al. | 514/44 |
| 6,194,388 B1 | 2/2001 | Krieg et al. | 514/44 |
| 6,207,646 B1 | 3/2001 | Krieg et al. | 514/44 |
| 6,214,806 B1 | 4/2001 | Krieg et al. | 514/44 |
| 6,225,292 B1 | 5/2001 | Raz et al. | |
| 6,239,116 B1 | 5/2001 | Krieg et al. | 514/44 |
| 6,534,062 B2 * | 3/2003 | Raz et al. | 424/193.1 |

FOREIGN PATENT DOCUMENTS

| | | |
|---|---|---|
| EP | 0 468 520 A2 | 1/1992 |
| EP | 855 184 | 1/1997 |
| GB | 1234718 | 9/1969 |
| WO | WO 96/02555 | 2/1995 |
| WO | WO 95/05853 | 3/1995 |
| WO | WO 95/26204 | 3/1995 |
| WO | WO 97/28259 | 8/1997 |
| WO | WO 98/18810 | 10/1997 |
| WO | WO 98/37919 | 2/1998 |
| WO | WO 98/16247 | 4/1998 |
| WO | WO 98/52962 | 11/1998 |
| WO | WO 01/35991 A2 | 5/2001 |

OTHER PUBLICATIONS

Krieg et al.; The role of CpG dinucleotides in DNA vaccines, 1998, Trends in Microbiology vol. 6, No. 1: 23–27.*

McCLuskie et. al.; Novel Strategies Using DNA for the Induction of Mucosal Immunity, 1999, Critical Reviews in Immunology 19:303–329.*

Hodes, T–cell–mediated regulation: Help and suppression, 1989, FUNDAMENTAL IMMUNOLOGY, pp. 587–620.*

Agrawal, et al. (1986). "Efficient methods for attaching non–radioactive labels to the 5' ends of synthetic oligodeoxyribonucleotides" *Nucleic Acids Res.* vol. 14: 6227–6245.

Ballas, Z.K., et al. (1996). "Induction of NK Activity in Murine and Human Cells by CpG Motifs in Oligodeoxynucleotides and Bacterial DNA", *Journal of Immunology,* vol. 157: 1840–1845.

Benoit, et al. (1987). "Strategies for antibody production and radioimmunoassays" *Neuromethods,* vol. 6: 43–72.

Bischoff, et al. (1987). "Introduction of 5'–terminal functional groups into synthetic oligonucleotides for selective immobilization" *Anal. Biochem.,* vol. 164: 336–344.

Blanks, et al. (1988). "An oligodeoxynucleotide affinity column for the isolation of sequence specific DNA binding proteins" *Nucleic Acids Res.,* vol. 16: 10283–10299.

Boujrad, et al. (1993). "Inhibition of hormone–stimulated steroidogenesis in cultured Leydig tumor cells by a cholesterol–linked phosphorothioate oligodeoxynucleotide antisense to diazepam–binding inhibitor" *Proc. Natl. Acad. Sci. USA,* vol. 90: 5728–31.

(List continued on next page.)

*Primary Examiner*—David Guzo
*Assistant Examiner*—Quang Nguyen
(74) *Attorney, Agent, or Firm*—Carol L. Francis; Paula A. Borden; Bozicevic, Field & Francis, LLP

(57) ABSTRACT

Immunostimulatory polynucleotide-immunomodulatory molecule conjugate compositions are disclosed. These compositions include a polynucleotide that is linked to an immunomodulatory molecule, which molecule comprises an antigen and may further comprise immunomodulators such as cytokines and adjuvants. The polynucleotide portion of the conjugate includes at least one immunostimulatory oligonucleotide nucleotide sequence (ISS). Methods of modulating an immune response upon administration of the polynucleotide-immunomodulatory conjugate preparation to a vertebrate host are also disclosed.

59 Claims, 7 Drawing Sheets

OTHER PUBLICATIONS

Branda, R.F., et al. (1996). "Amplification of antibody production by phosphorothioate oligodeoxynucleotides" *The J. of Laboratory & Clinical Medicine*, vol. 128(3): 329–338.

Connolly (1985). "Chemical synthesis of oligonucleotides containing a free sulphydryl group and subsequent attachment of thiol specificprobes" *Nucleic Acids Res.*, vol. 13: 4485–4502.

Connolly (1987). "The synthesis of oligonucleotides containing a primary amino group at the 5'–terminus" *Nucleic Acids Res.*, vol. 15: 3131–3139.

Corey, et al. (1987). "Generation of a hybrid sequence–specific single–stranded deoxyribonucleotide" *Science*, vol. 238: 1401–1403.

Coull, et al.(1986). "A novel method for the introduction of an aliphatic primary amino group at the 5' terminus of synthetic oligonucleotides" *Tetrahedron Lett.*, vol. 27: 3991–3994.

Czerkinsky, et al. (1989). "Oral administration of a streptococcal antigen coupled to cholera toxin B subunit evokes strong antibody responses in salivary glands and extramucosal tissues" *Infect. Immun.*, vol. 57: 1072–1077.

Dertzbaugh et al. (1993). "Comparative effectiveness of the cholera toxin B subunit and alkaline phosphatase as carriers for oral vaccines" *Infect. Immun.*, vol. 61: 48–55.

Geoghegan et al., (1992). "Site–directed conjugation of nonpeptide groups to peptides and proteins via periodate oxidation of a 2–amino alcohol. Application to modification at N–terminal serine" *Bioconjug. Chem.*, vol. 3: 138–146.

Goodchild (1990). "Conjugates of oligonucleotides and modified oligonucleotides: A review of their synthesis and properties" *Bioconjugate Chem.*, vol. 1: 165.

Grabarak, et al. (1990). "Zero–length crosslinking procedure with the use of active esters" *Anal Biochem.*, vol. 185: 131–135.

Haralambidis, et al.(1990). "The synthesis of polyamide–oligonucleotide conjugate molecules" *Nucleic Acids Res.*, vol. 18: 493–499.

Haralambidis, et al.(1990). "The preparation of polymide–oligonucleotide probes containing multiple non–radioactive" *Nucleic Acids Res.*, vol. 18: 501–505.

Kämper, et al. (1989). "New recombinant linear DNA–elements derived from *Kluyveromyces lactis* killer plasmids" *Nucleic Acids Res.*, vol. 17: 1781–1794.

Kessler (1992). "Nonradioactive Labeling Methods for Nucleic Acids" in L.J. Kricka (ed) *Nonisotopic DNA Probe Techniques*, Academic Press, pp. 29–87.

Kremsky, et al. (1987). "Immobilization of DNA via oligonucleotides containing aldehyde or carboxylic acid group at the 5' terminus" *Nucleic Acids Res.*, vol. 15: 2891–2902.

Krieg, et al.(1989). "A role for endogenous retroviral sequences in the regulation of lymphocyte activation" *J. Immunol.*, vol. 1443: 2448–2451.

Krieg, et al. (1995). "CpG motifs in bacterial DNA trigger direct B–cell activation" *Nature*, vol. 374: 546–549.

Krieg, et al.(1996). "Oligodeoxynucleotide modifications determine the magnitude of B cell stimulation by CpG motifs" *Antisense Nucl. Acid Drug Dev.*, vol. 6: 133–139.

Kreig, et al.(1996). "Lymphocyte activation by CpG dinucleotide motifs in prokaryotic DNA" *Trends in Microbiol.*, vol. 4: 73–77.

Nashar, et al.(1993). "Current progress int eh development of the B subunits of cholera toxin and *Escherichia coli* heat–labile enerotoxin as carriers for the oral delivery of heterologous antigens and epitopes" *Vaccine*, vol. 11: 235–240.

O'Shannessy, et al.(1985). "Specific conjugation reactions of the oligosaccharide moieties of immunoglobins" *J. Applied Biochem.*, vol. 7: 347–355.

Raz et al.(1996). "Potential role of immunostimulatory DNA sequences (ISS) in genetic immunization and autoimmunity" *Arthritis & Rhuematism*, vol. 39(9): 615.

Raz et al. (1996). "Preferential Induction of a Th1 Immune Response and Inhibition of Specific IgE Antibody Formation by Plasmid DNA Immunization", *Proceedings of the Natl Academy of Sci. USA*, vol. 93: 5141–5145.

Roget, et al. (1989). "Synthesis and use of labelled nucleoside phosphoramidite building blocks bearing a reporter group: biotinyl, dinitrophenyl, pyrenyl, and dansyl" *Nucleic Acids Res.*, vol. 17: 7643–7651.

Ruth (1991). "Oligodeoxynucleotides with reporter groups attached to the base" in *Oligonucleotides and Analogues: A Practical Approach.* Eckstein (ed.) IRL Press pp. 255–283.

Ruth. "Chemical synthesis of non–radioactively–labeled DAN hybridization probes" *Fourth Annual Congress for Recombinant DNA Research* p. 123.

Sato et al. (1996). "Immunostimulatory DNA sequences necessary for effective intradermal gene immunization" *Science*, vol. 273: 352–354.

Sinah, et al.(1991). "Oligonucleotides with reporter groups attached to the 5' terminus" *Oligonucleotide Analogues: A Practical Approach.* Eckstien (ed.) IRL Press pp. 185–210.

Staros, et al.(1986). "Enhancement by N–Hydroxysulfosuccinimide of water–soluble carbodiimide–mediated coupling reactions" *Anal Biochem.*, vol. 156: 220–222.

Warren. "Adjuvants" in *Encyclopedia of Immunology.* Roitt et al. (eds.) Academic Press. pp. 28–30.

Yanagawa, et al.(1988). "Analysis of superhelical structures of nucleic acid–lipid conjugates by image processing" *Nucleic Acids Symp. Ser.*, vol. 19: 189–192.

Zuckermann, et al. (1987). "Efficient methods for attachment of thiol specific probes to the 3'–ends of synthetic oligodeoxynucleotides" *Nucleic Acids Res.*, vol. 15: 5305–5321.

Bennett et al. (1985), "DNA Binding to Human Leukocytes." *The American Society for Clinical Investigation, Inc.*, 2182–2190.

Branda et al. (1993). "Immune Stimulation by an Antisense Oligomer Complementary to the rev Gene of HIV–1" *Biochem. Pharmacol.*, vol. 45:2037–2043.

Carlberg (1993), "Rxr–independent Action of the Receptors for Thyroid Hormone, Retinoid Acid and Vitamin D on Inverted Palindromes." *Biochemical and Biophysical Research Communications*, vol. 195(3):1345–1353.

Chace et al. (1997) "Bacterial DNA–Induced NK Cell IFN–γ Production is Dependent on Macrophage Secretion of IL–12" Clinical Immunology and Immunopathology. *Clinical Immunology and Immunopathology*, vol. 84(2):185–193.

Chu et al. (1997) CpG oligodeoxynucleotides Act as Adjuvants that switch on T helper 1 (Th1) Immunity, J. Exp. Med., *The Rockefeller University Press*, vol. 186(10):1623–1631.

Corry et al. (1996), "Interleukin 4, but not Interleukin 5 or Eosinophils, Is Required in a Murine model of Acute Airway Hyperreactivity." *J. Exp. Med.*, vol. 183:109–117.

Cowdery et al. (1996) "Bacterial DNA induces NK cells to produce IFN-γ in vivo and increases the toxicity of lipopolysaccharides." *J. Immunol.*, vol. 156:4570–4575.

Davis "Plasmid DNA expression systems for the purpose of immunization." Curr Opin Biotechnol. 8: 635–640, 1997.

Davis et al. (1993), "Plasmid DNA Is Superior to Viral Vectors for Direct Gene Transfer into Adult Mouse Skeletal Muscle." *Human Gene Therapy*, vol. 4:733–740.

Ewel et al. (1992), "Polyinosinic–Polycytidylic Acid complexed with Poly–L–lysine and Carboxymethylcellulose in Combination with Interleukin 2 in Patients with Cancer: Clinical and Immunological Effects." *Cancer Research*, vol. 52:3005–3010.

Feltquate et al. (1997), "Different T Helper Cell Types and Antibody Isotypes Generated by Salinea nd Gene Gun DNA Immunization." *The Journal of Immunology*, vol. 158:2278–2284.

Fuller et al. (1994), "A Qualitative Progression in HIV Type 1 Glycoprotein 120–Specific Cytotoic Cellular and Humoral Immune Response in Mice Receiving a DNA–Based Glycoprotein 120 Vaccine." *AIDS Research and Human Retrviruses*, vol. 10(11):1433–1441.

Gray et al. (1997) "Immune cell involvement in anti–c–myc DNA prevention of tumor formation in a mouse model of Burkitt's lyphoma." *Nucleosides & Nucleotides*, vol. 16(7–9):1727–1730.

Hartmann et al. (2000) "Mechanism and Function of a Newly Identified CpG DNA Motif in Human Primary B Cells." *The Journal of Immunology*, vol. 164:944–952.

Hawkins et al. Editorial "Toward Genetically Targeted Research and therapeutics." *Antisense Research and Development*, p. 185.

Hohlfeld et al. (1994), "The Immunobiology of Muscle." *Immunology Today*, vol. 15(6):269–274.

Hsu et al. (1996) "Immunoprophylaxis of allergen–induced immunoglobulin E synthesis and airway hyperresponsiveness in vivo by genetic immunization." *Nature Med.*, vol. 2(5):540–544.

Iguchi–Ariga et al. (1989), "CpG methylation of the camp–responsive enhancer/promoter sequence TGACGTCA abolishes specific factor binding as well as transcriptional activation." *Genes & Development*, vol. 3:612–619.

Jachimczak et al. (1993), "The effect of transforming growth factor–$\beta_2$–specific phosphorothrioate–anti–sense oligodeoxynucleotides in reversing cellular immunosuppression in malignant glioma." *J. Neurosurg*, vol. 78:944–951.

Jyonouchi et al. (1993), "Immunomodulating Actions of Nucleotides: Enchancement of Immunoglobulin Production by Human Cord Blood Lymphocytes." *Pediatric Research*, vol. 34(5):565–571.

Kataoka et al. (1992). "Antitumor Activity of Synthetic Oligonucleotides with Sequences from cDNA Encoding Proteins of Mycobacterium bovis BCG" Jpn. J. Cancer Res., vol. 83:244–247.

Kemeny et al. (1992), "CD8+ T cells in allergy." *Allergy*, vol. 47:12–21.

Kimura et al. (1994). "Binding of Oligoguanylate to Scavenger Receptors is Required for Oligonucleotides to Augment NK Cell Activity and Induce IFN," *J. Biochem.*, vol. 116:991–994.

Kline et al. (1997). "Immune redirection by CpG oligonucleotides: conversion of a Th2 response to a Th1 response in a murine model of asthma" *J. Invest. Med.*, vol. 45(3): 282A.

Klinman et al. (1996). "Contribution of CpG motifs to the immunogenicity of DNA vaccines" *J. Immunol.*, vol. 158: 3635–3639.

Klinman et al. (1996). "CpG Motifs Present in Bacterial DNA Rapidly Induce Lymphocytes to Secrete Interleukin 6, Interleukin 12, and Interferon γ" *Proc. Natl. Acad. Sci. USA.*, vol. 93: 2879–2883.

Krieg (1995), "CpG DNA: A Pathogenic Factor in Systemic Lupus Erythematosus?" *Journal of Clinical Immunology*, vol. 15(6):284–292.

Kuramoto et al. (1992). Oligonucleotide sequences required for natural killer cell activation. Jpn. J. Cancer Res., vol. 83: 1128–1131.

Leclerc et al. (1997). "The preferential induction of a Th1 immune response by DNA based immunization is mediated by the immunostimulatory effect of plasmid DNA" Cell. Immunol., vol. 179:97–106.

Lee et al. (1997), "Inhibition of IgE antibody Formation by Plasmid DNA Immunization Is Mediated by both CD4+ and CD8+ T Cells." *Int. Arch. Allergy Immunol*, vol. 113:227–230.

Liang et al. (1996) "Activation of Human B Cells by Phosphorothioate Oligodeoxynucleotides." *J. Clin. Invest.*, vol. 98(5):1119–1129.

Lipford et al. (1997). "CpG–containing synthetic oligonucleotides promote B and cytotoxic T cell responses to protein antigen: a new class of vaccine adjuvant" Eur. J. Immunol., vol. 27:2340–2344.

MacFarlane et al. (1997) "Unmethylated CpG– containing oligodeoxynucleotides inhibit apoptosis in WEHI 231B lymphocytes induced by several agents; evidence for blockade of apoptosis at a distal signaling stop." *Immunology*, vol. 91:586–593.

Mader et al. (1993), "A steroid–inducible promoter for the controlled overexpression of cloned genes in eukaryotic cells." *Proc. Natl. Acad. Sci.*, vol. 90:5603–5607.

Manickan et al. (1997), "Enhancement of immune response to naked DNA vaccine by immunization with transfected dendritic cells." *Journal of Leukocyte Biology*, vol. 61(2):125–132.

Messina et al. (1991), "Stimulation of in vitro Murine Lymphocyte Proliferation by Bacterial DNA." *The Journal of Immunology*, vol. 147:1759–1764.

Messina et al. (1993) "The Influence of DNA Structure in the in–vitro Stimulation of Murine Lymphocytes by Natural and Synthetic Polynucleotide Antigens." *Cellular Immunology*, vol. 147: 148–157.

Mojcik et al. (May 1993), "Administration of a Phosphorothioate Oligonucleotide Antisense to Murine Endogenous Retroviral MCF env Causes Immune Effects in Vivo in a Sequence–Specific Manner," *Clinical Immunology and Immunopathology*, vol. 67(2):130–136.

Mor et al. (1995) "Complexity of the Cytokine and Antibody Response Elicited by Immunizing Mice with Plasmodium yoelii Circumsporozoite protein plasmid DNA." *The Journal of Immunology*, vol. 155(4);2039–2046.

Mulligan (1993). "The Basic Science of Gene Therapy" Science, vol. 260: 926–932.

MULTI–TEST:product insert (1984) *Lincoln Diagnostics, Inc.*, pp. 1–6.

Nakagawa et al. (1993), "Immunotherapy of Allergic Diseases." *Int. Arch Allergy Immunol.*, vol. 102:117–120.

Nishida et al. (1990), "Definition of a GC–rich motif as regulatory sequence of the human IL–3 gene: coordinate regulation of the IL–3 gene by CLE2/GC box of the GM–CSF gene in T cell activation." *International Immunology,* vol. 3(3):245–254.

Ohi et al. (1990). "Construction and Replication of an Adeno–Associated Virus Expression Vector that Contain Human Beta–globin cDNA" Gene, vol. 89(2): 279–282.

Pardoll et al. (1995), "Exposing the Immunology of Naked DNA Vaccines." *Immunity,* vol. 3(2):165–169.

Pisetsky (1996). "Immune activation by bacterial DNA: a new genetic code" *Immunity,* vol. 5: 5(4):303–10.

Pisetsky et al. (1994), "Stimulation of Murine Lymphocyte Proliferation by a Phosphorothioate Oligonucleotide with Antisense Activity for Herpes Simplex Virus," *Life Sciences,* vol. 54:101–107.

Pisetsky et al. (1995), "Immunological Properties of Bacterial DNA," *Ann. NY Acad. Sci.,* vol. 772:152–163.

Pisetsky, D. (1996), "The Immunologic Properties of DNA," *Journal of Immunology,* vol. 156(2):558–564.

Ramsay et al. (1994), "Enhancement of Mucosal IgA Responses by Interleukins 5 and 6 Encoded in Recombinant Vaccine Vectors." *Reproduction, Fertility, and Development,* vol. 6(3):389–392.

Raz et al. (1994), "Intradermal Gene Immunization: The Possible Role of DNA Uptake in the Induction of Cellular Immunity to Viruses," *Proc. Natl. Acad. Sci. USA,* vol. 91:9519–9523.

Raz, et al., "Potential Role of Immunostimulatory DNA sequences in genetic immunization and autoimmunity" Oct. 20, 1996, XP–002058356.

Robinson et al. (1993), "Use of Direct DNA Inoculations to Elicit Protective Immune Responses." *Journal of Cellular Biochemistry, Supplement* 17D:85, 92.

Romagnani (1994). "Lymphokine Production by Human T Cells in Disease States" *Annu. Rev. Immunol.,* vol. 12: 227–257.

Roman et al. (1997). "Immunostimulatory DNA Sequences Function as T helper–1–promoting Adjuvants" *Nat. Med.,* vol. 3: 849–854.

Sano et al. (1989), "Binding Properties of Human Anti–DNA Antibodies to Cloned Human DNA Fragments." *Scand. J. Immunol.,* vol. 30:51–63.

Schleimer et al. (1992), "IL–4 Induces Adherence of Human Eosinophils and Basophils but not Neutrophils to Endothelium." *The Journal of Immunology,* vol. 148(4):1086–1092.

Schwartz et al. (1997) CpG Motifs in Bacterial DNA Cause Inflammation in the Lower respiratory Tract, *The Journal of clinical investigation,* vol. 100(1):68–73.

Secrist et al. (1993), "Allergen Immunotherapy Decreases Interleukin 4 Production in CD4+ T Cells from Allergic Individuals." *J. Exp. Med.,* vol. 178:2123–2130.

Sedegah et al. (1994) "Protection Against Malaria by Immunization with Plasmid DNA encoding Circumsporoite Protein." *Proc. Natl. Acad. Sci. USA,* vol. 91:9866–9870.

Shiver et al. (1995) "Cytotoxic T Lymphocyte and Helper T Cell Responses following HIV Polynucleotide Vaccination, DNA Vaccines, A New Era in Vaccinology" *The NY Academy of Sciences,* vol. 772:198–209.

Sonehara et al. (1996). "Hexamer Palindromic Oligonucleotides with 5'–CG–3' Motif(s) Induce Production of Interferon" *Journal of Interferon and Cytokine Research,* vol. 16: 799–803.

Sparwasser et al. (1997), "Bacterial DNA causes septic shock." *Nature,* vol. 386(6623):336–337.

Spier (1996). "International Meeting on the Nucleic Acid Vaccines for the Prevention of Infectious Diseases and Regulating Nucleic Acid (DNA) vaccines." *Vaccine,* vol. 14(13):1258–1288.

Stacey et al. (1996). "Macrophages ingest and are activated by bacterial DNA" *J. Immunol.,* vol. 157: 2116–2122.

Tam et al. (1997), "Oligonucleotide–Mediated Inhibition of CD28 Expression Induces Human T Cell Hyporesponsiveness and Manifests Impaired Contact Hypersensitivity in Mice." *The Journal of Immunology,* vol. 158(1):200–208.

Tanaka et al. (1992). "An Antisense Oligonucleotide Complementary to a Sequence in Iγ2b Increases γ2b Germline Transcripts, Stimulates B Cell DNA Synthesis, and Inhibits Immunoglobulin Secretion." *The Journal of Experimental Medicine,* vol. 175:597–607.

Terr, "Allergy Desensitization." Chapter 56:739–743, 1993.

Tokunaga et al. (1992), "Synthetic Oligonucleotides with Particular Base Sequences from the cDNA Encoding Proteins of *Mycobacterium bovis* BCG Induce Interferons and Activate Natural Killer Cells" *Microbiol. Immunol.,* vol. 36(1): 55–66.

Trinchieri et al. (1994). "The role of interleukin 12 in the immune response, disease, and therapy" *Immunology Today,* vol. 15(10): 460–463.

Ulmer et al. (1993) "Heterologous protection against influenza by injection of DNA encoding a viral protein." *Science,* vol. 259:1745–1748.

Verma et al. (1997). "Gene therapy–promises, problems, and prospects" *Nature,* vol. 389: 239–242.

Weiner et al. (1997). "Immunostimulatory oligodeoxynucleotides containing the CpG motif are effective as immune adjuvants in tumor antigen immunization" *Proc. Natl. Acad. Sci. USA,* vol. 94: 10833–10837.

Whalen et al. (1995). "DNA–Mediated Immunization of the Hepatitis B Surface Antigen," *Ann. NY Acad. Sci.,* vol. 772:64–76.

Wooldridge et al. (1997) "Immunostimulatory Oligodeoxynucleotides Containing CpG Motifs Enhance the Efficacy of Monoclonal Antibody Therapy of Lymphoma." *Blood,* vol. 89(8):2994–2998.

Xu et al. (1994) "Protection Against Leishmaniasis by Injfection of DNA encoding a major surface glycoprotein, gp63, of L. Major." *Immunology,* p. 173–176.

Yakubov et al. (1989), "Mechanism of oligonucleotide uptake by cells: Involvement of specific receptors?" *Proc. Natl. Acad. Sci.,* vol. 86:6454–6458.

Yamamoto (1994), "Mode of Action of Oligonucleotide Fraction Extracted from *Mycobacterium Bovis* BCG." *Kekkaku,* vol. 69(9):29–32.

Yamamoto et al. (1994), "Lipofection of Synthetic Oligodeoxyribonucleotide Having a Palindromic Sequence of AACGTT to Murine Splenocytes Enhances Interferon Production and natural Killer Activity," *Microbiol. Immunol.,* vol. 38(10):831–836.

Yamamoto et al. (1994). "Ability of Oligonucleotides with Certain Palindromes to Induce Interferon Production and Augment Natural Killer Cell Activity is Associated with their Base Length" *Antisense Research and Development,* vol. 4: 119–122.

Yamamoto et al. (1994). "Synthetic oligonucleotides with certain Palindromes stimulate interferon production of human peripheral blood lymphocytes" *Jpn. Cancer Res.* vol. 85: 775–779.

Yamamoto et al. (Jun. 15, 1992), "Unique Palindromic Sequences in Synthetic Oligonucleotides are Required to Induce INF and Augment INF–Mediated Natural Killer Acitivty," *Jornal of Immunology,* vol. 148(12):4072–4076.

Yi et al. (1996), "IFN–γ Promotes IL–6 and IgM Secretion in Response to CpG Motifs in Bacterial DNA and Oligodeoxynucleotides," *Journal of Immunology,* vol. 156:558–564.

Yi et al. (1996), "Rapid Immune Activation by CpG Motifs in Bacterial DNA" *J. Immunol.,* vol. 157(12): 5394–5402.

Zhao et al. (1993), "Comparison of Cellular Binding and Uptake of Antisense Phosphodiester, Phosphorothioate, and Mixed Phosphorothioate and Methylphosphonate Oligonucleotides." *Antisense Research and Development,* vol. 3:53–66.

* cited by examiner

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: DY1018 polynucleotide

<400> SEQUENCE: 1
tgactgtgaa cgttcgagat ga                    22

<210> SEQ ID NO 2
<211> LENGTH: 22
<212> TYPE: DNA
<213> ORGANISM: Artificial Sequence
<220> FEATURE:
<223> OTHER INFORMATION: D41019 polynucleotide

<400> SEQUENCE: 2
tgactgtgaa ggttggagat ga                    22

IMMUNOSTIMULATORY POLYNUCLEOTIDE/ IMMUNOMODULATORY MOLECULE CONJUGATES

RELATED U.S. PATENT APPLICATIONS

This is a continuation-in-part and utility conversion of U.S. Provisional Patent Application Ser. No. 60/028,118, filed Oct. 11, 1996.

STATEMENT OF FEDERALLY SPONSORED RESEARCH

Support for the research disclosed herein may have been provided by the National Institutes of Health under Grant Nos. AI37305 and/or AR25443.

FIELD OF THE INVENTION

The invention relates to compositions comprising an immunomodulatory molecule (IMM) including an antigen, conjugated to a polynucleotide that contains or consists of at least one immunostimulatory oligonucleotide (ISS-PN). It also relates to methods for modulating the immune response of a vertebrate host to an antigen.

HISTORY OF THE RELATED ART

Conventionally, immunization of a host against an antigen is accomplished by repeatedly vaccinating the host with the antigen. While most current vaccines elicit reasonable antibody responses, cellular responses (in particular, major histocompatibility complex (MHC) class I-restricted cytotoxic T cells) are generally absent or weak. For many infectious diseases, such as tuberculosis and malaria, humoral responses are of little protective value against infection.

Given the weak cellular immune response to protein antigens, modulation of the immune responses to these antigens has clear importance. The ability to modify immune responses to protein or peptide antigen has implications for tumor therapy, for the treatment of allergic disorders and for treatment of other conditions achievable through induction of a vigorous cellular immune response.

SUMMARY OF THE INVENTION

The present invention provides compositions comprising an ISS-PN which is conjugated to an IMM (which includes an antigen) to form ISS-PN/IMM conjugates. The ISS-PN/IMM conjugates of the invention are biological response modifiers in the sense that they modify the humoral and cellular immune response of a host to an antigen.

Specifically, the ISS-PN and IMM components of the ISS-PN/IMM conjugates synergistically boost the magnitude of the host immune response against an antigen to a level greater than the host immune response to either the IMM, antigen or ISS-PN alone. The ISS-PN/IMM conjugates also shift the host cellular immune response away from the helper T lymphocyte type 2 (Th2) phenotype toward a helper T lymphocyte type 1 (Th1) phenotype. These responses to ISS-PN/IMM conjugates are particularly acute during the important early phase of the host immune response to an antigen.

To these ends, ISS-PN/IMM conjugates are delivered by any route through which antigen-sensitized host tissues will be contacted with the ISS-PN/IMM conjugate. ISS-PN/IMM conjugates administered in this fashion boost both humoral (antibody) and cellular (Th1 type) immune responses of the host. Thus, use of the method to boost the immune responsiveness of a host to subsequent challenge by a sensitizing antigen without immunization avoids the risk of Th2-mediated, inmmunization-induced anaphylaxis by suppressing IgE production in response to the antigen challenge. An especially advantageous use for this aspect of the invention is treatment of localized allergic responses in target tissues where the allergens enter the body, such as the skin and mucosa.

Suppression of the Th2 phenotype according to the invention is also a useful in reducing antigen-stimulated IL-4 and IL-5 production. Thus, the invention encompasses delivery of ISS-PN/IMM conjugates to a host to suppress the Th2 phenotype associated with conventional antigen immunization (e.g., for vaccination or allergy immunotherapy).

The shift to a Th1 phenotype achieved according to the invention is accompanied by increased secretion of IFN $\alpha$, $\beta$ and $\gamma$, as well as IL-12 and IL-18. Each of these cytokines enhance the host's immune defenses against intracellular pathogens, such as viruses. Thus, the invention encompasses delivery of ISS-PN/IMM conjugates to a host to combat pathogenic infection.

Angiogenesis is also enhanced in the Th1 phenotype (ostensibly through stimulation by IL-12). Thus, the invention encompasses delivery of ISS-PN/IMM conjugates to a host to stimulate therapeutic angiogenesis to treat conditions in which localized blood flow plays a significant etiological role; e.g., retinopathies.

The ISS-PN/IMM conjugates of the invention comprise an IMM conjugated to a polynucleotide that includes, or consists of, at least one immunostimulatory oligonucleotide (ISS-ODN) moiety. The ISS-ODN moiety is a single- or double-stranded DNA or RNA oligonucleotide having at least 6 nucleotide bases which may include, or consist of, a modified oligonucleoside or a sequence of modified nucleosides.

The ISS-ODN moieties comprise, or may be flanked by, a CpG containing nucleotide sequence or a p(IC) nucleotide sequence, which may be palindromic. Where the oligonucleotide moiety comprises a CpG sequence, it may include a hexamer structure consisting of: 5'-Purine, Purine, CG, Pyrimidine, Pyrimidine-3'. Examples of such hexamer structures are AACGTT, AGCGTT, GACGTT, GGCGTT, AACGTC, and AGCGTC.

In one aspect of the invention, the ISS-PN consists of an ISS-ODN. Alternatively, the ISS-PN comprises an ISS-ODN.

Conjugates of the invention also include PN/IMM wherein the PN serves as a carrier to introduce the IMM antigen into MHC Class I processing pathways not normally stimulated by soluble antigen, but lacks ISS activity and therefore does not stimulate a Th1 phenotype immune response. Examples of such PN/IMM are those wherein the CpG motif is mutated, for example, to a GpG motif.

In one aspect of the invention, the IMM conjugate partner to the ISS-PN consists of an antigen. Such antigens are selected from the group of antigens consisting of proteins, peptides, glycoproteins, polysaccharides and gangliosides.

In another aspect of the invention, the IMM conjugate partner comprises an antigen and further comprises an immunostimulatory molecule selected from the group of such molecules consisting of adjuvants, hormones, growth factors, cytokines, chemokines, targeting protein ligands, and trans-activating factors.

In another aspect of the invention, the ISS-PN/IMM conjugate is modified for targeted delivery by, for example, attachment to a monoclonal antibody, receptor ligand and/or liposome.

Pharmaceutically acceptable compositions of ISS-PN/IMM conjugates are provided for use in practicing the methods of the invention. Where appropriate to the contemplated course of therapy, the ISS-PN/IMM conjugates may be administered with anti-inflammatory or immunotherapeutic agents. Thus, a particularly useful composition for use in practicing the method of the invention is one in which an anti-inflammatory agent (e.g., a glucocorticoid) is mixed with, or further conjugated to, an ISS-PN/IMM conjugate.

The ISS-PN/IMM conjugates can also be provided in the form of a kit comprising ISS-PN/IMM conjugates and any additional medicaments, as well as a device for delivery of the ISS-PN/IMM conjugates to a host tissue and reagents for determining the biological effect of the ISS-PN/IMM conjugates on a treated host.

DETAILED DESCRIPTION OF THE INVENTION

Figure 1:
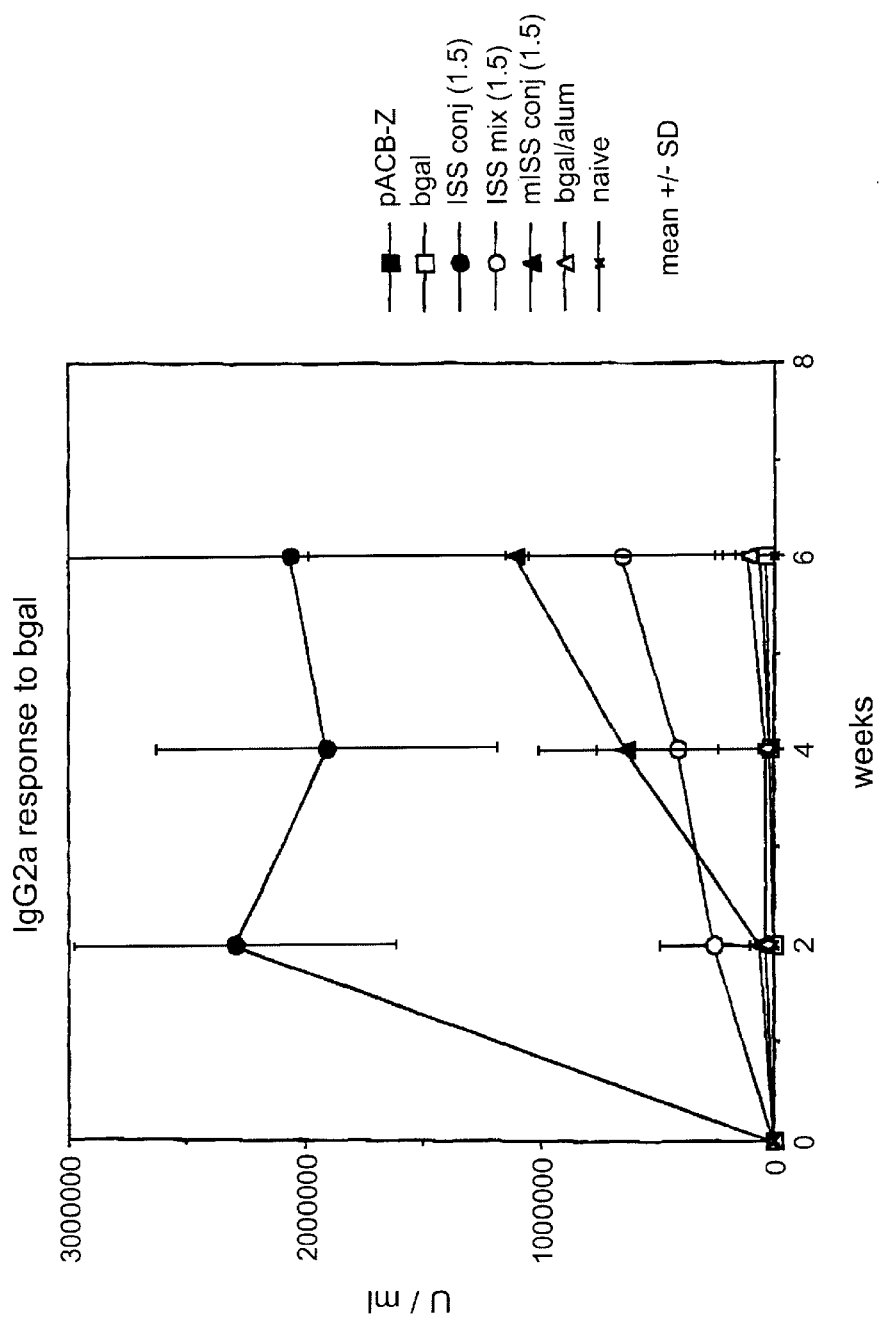
FIG. 1 is a graph of data demonstrating the vigorous Th1-type immune response (as measured by production of IgG2a against an IMM antigen) stimulated by ISS-PN/IMM (1:5 ratio) in comparison to the levels of Th2-like responses stimulated by an ISS containing, antigen encoding plasmid (pACB-Z); the antigen alone (β-gal); the antigen mixed with an ISS (1:5 ratio); the antigen conjugated to a non-stimulatory PN (mISS conj; 1:5 ratio); the antigen in adjuvant (alum) and, for reference, the IgG2a levels in naive (unexposed) mice. The horizontal axis represents the levels (units/ml) of antibody; the vertical axis represents the number of weeks following primary antigen exposure.

A. Biological Activity of the ISS-PN/IMM Conjugates

The immune response stimulated by the ISS-PN/IMM conjugates of the invention differs from the vertebrate immune response to conventional vaccination in both magnitude and quality. In the former respect, the host immune response to an antigen is boosted to a level greater than achieved on exposure to an ISS-PN or antigen administered alone or together in an unconjugated form. Thus, one surprising aspect of the invention is that conjugation of an ISS-PN to an antigen-containing IMM produces a synergism between the immunostimulatory activity of the ISS-PN and the immunomodulatory activity of the IMM that immunizes the host to the antigen more effectively than one would predict.

Advantageously, the immune response stimulated according to the invention differs from the immune response of vertebrates to conventional vaccination in that the latter develops in a Th2 phenotype while the former develops in a Th1 phenotype. In this regard, it is helpful to recall that CD4+ lymphocytes generally fall into one of two distinct subsets; i.e., the Th1 and Th2 cells. Th1 cells principally secrete IL-2, IFNγ and TNFβ (the latter two of which mediate macrophage activation and delayed type hypersensitivity) while Th2 cells principally secrete IL-4 (which stimulates production of IgE antibodies), IL-5 (which stimulates granulocyte infiltration of tissue), IL-6 and IL-10. These CD4+ subsets exert a negative influence on one another; i.e., secretion of Th1 lymphokines inhibits secretion of Th2 lymphokines and vice versa.

Factors believed to favor Th1 activation resemble those induced by viral infection and include intracellular pathogens, exposure to IFN-β, IFN-α, IFNγ, IL-12 and IL-18 and exposure to low doses of antigen. Th1 type immune responses also predominate in autoimmune disease. Factors believed to favor Th2 activation include exposure to IL-4 and IL-10, APC activity on the part of B lymphocytes and high doses of antigen.

Active Th1 (IFNγ) cells enhance cellular immunity and are therefore of particular value in responding to intracellular infections, while active Th2 cells enhance antibody production and are therefore of value in responding to extracellular infections (at the risk of anaphylactic events associated with IL-4 stimulated induction of IgE antibody production). Thus, the ability to shift host immune responses from the Th1 to the Th2 repertoire and vice versa has substantial clinical significance for controlling host immunity against antigen challenge (e.g., in infectious and allergic conditions).

To that end, the methods of the invention shift the host immune response to a sensitizing antigen toward a Th1 phenotype (Example I). Consequently, Th2 associated cytokine production and antigen stimulated production of IgE (Examples II and III) are suppressed, thereby reducing the host's risk of prolonged allergic inflammation and minimizing the risk of antigen-induced anaphylaxis. CTL production is also stimulated to a greater degree in animals treated according to the invention. Because CTL production is tied to antigen processing in Class I MHC pathways, increased CTL production can be produced from non-immunostimulatory PN/IMM as well as ISS-PN/IMM (Example IV).

Although the invention is not limited to any particular mechanism of action, it is conceivable that PN facilitate uptake of exogenous antigen by antigen presenting cells for presentation through host MHC Class I processing pathways not normally stimulated by soluble antigen. Thus, ISS-PN/IMM carry antigen into MHC Class I processing pathways (which may also be achieved by PN/IMM without ISS activity) then stimulate a cytokine cascade in a Th1 phenotype (as a result of ISS activity). Whatever the mechanism of action, use of ISS-PN/IMM to boost the host's immune responsiveness to a sensitizing antigen and shift the immune response toward a Th1 phenotype avoids the risk of immunization-induced anaphylaxis, suppresses IgE production in response to a sensitizing antigen and eliminates the need to identify the sensitizing antigen for use in immunization.

With reference to the invention, "boosting of immune responsiveness in a Th1 phenotype" in an ISS-PN/IMM treated host is evidenced by:

(1) a reduction in levels of IL-4 measured before and after antigen-challenge; or detection of lower (or even absent) levels of IL-4 in a treated host as compared to an antigen-primed, or primed and challenged, control;

(2) an increase in levels of IL-12, IL-18 and/or IFN (α, β or γ) before and after antigen challenge; or detection of higher levels of IL-12, IL-18 and/or IFN (α, β or γ) in an ISS-PN/IMM treated host as compared to an antigen-primed or, primed and challenged, control;

(3) IgG2a antibody production in a treated host; or (4) a reduction in levels of antigen-specific IgE as measured before and after antigen challenge; or detection of lower (or even absent) levels of antigen-specific IgE in an ISS-PN/IMM treated host as compared to an antigen-primed, or primed and challenged, control.

Exemplary methods for determining such values are described further in the Examples.

Thus, the ISS-PN/IMM conjugates of the invention provide relatively safe, effective means of stimulating a robust immune response in a vertebrate host against any antigen.

B. ISS-PN/IMM Conjugates: Structure and Preparation

1. ISS-PN Root Structure

The ISS-ODN base of the ISS-PN/IMM conjugates of the invention includes an oligonucleotide, which may be a part of a larger nucleotide construct such as a plasmid. The term "polynucleotide" therefore includes oligonucleotides, modified oligonucleotides and oligonucleosides, alone or as part of a larger construct. The polynucleotide may be single-stranded DNA (ssDNA), double-stranded DNA (dsDNA), single-stranded RNA (ssRNA) or double-stranded RNA (dsRNA).

The polynucleotide portion can be linearly or circularly configured, or the oligonucleotide portion can contain both linear and circular segments. Modifications of oligonucleotides include, but are not limited to, modifications of the 3'OH or 5'OH group, modifications of the nucleotide base, modifications of the sugar component, and modifications of the phosphate group.

The oligonucleotide base of ISS-PN/IMM conjugates may comprise ribonucleotides (containing ribose as the only or principal sugar component), deoxyribonucleotides deoxyribose as the principal sugar component), or in accordance with established state-of-the-art modified sugars or sugar analogs may be incorporated in the oligonucleotide of the present invention. Thus, in addition to ribose and deoxyribose, the sugar moiety may be pentose, deoxypentose, hexose, deoxyhexos, glucose, arabinose, xylose, lyxose, and a sugar "analog" cyclopentyl group. The sugar may be in pyranosyl or in a furanosyl form. In the modified oligonucleotides of the present invention the sugar moiety is preferably the furanoside of ribose, deoxyribose, arabinose or 2'-0-methylribose, and the sugar may be attached to the respective heterocyclic bases either in I or J anomeric configuration. The preparation of these sugars or sugar analogs and the respective "nucleosides" wherein such sugars or analogs are attached to a heterocyclic base (nucleic acid base) per se is known, and need not be described here, except to the extent such preparation may pertain to any specific example.

The phosphorous derivative (or modified phosphate group) which may be attached to the sugar or sugar analog moiety in the modified oligonucleotides of the present invention may be a monophosphate, diphosphate, triphosphate, alkylphosphate, alkanephosphate, phosphoronthioate, phosphorodithioate or the like. The preparation of the above-noted phosphate analogs, and their incorporation into nucleotides, modified nucleotides and oligonucleotides, per se, is also known and need not be described here.

The heterocyclic bases, or nucleic acid bases which are incorporated in the oligonucleotide base of the ISS-PN/IMM conjugates may be the naturally occurring principal purine and pyrimidine bases, (namely uracil or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) have become available in the prior art, such that oligonucleotide base of the ISS-PN/IMM conjugates may include one or several heterocyclic bases other than the principal five base components of naturally occurring nucleic acids. Preferably, however, the heterocyclic base in the oligonucleotide base of the ISS-PN/IMM conjugates is selected form uracil-5-yl, cytosin-5-yl, adenin-7-yl, adenin-8-yl, guanin-7-yl, guanin-8-yl, 4-aminopyrrolo [2.3-d]pyrimidin-5-yl, 2-amino-4-oxopyrolo[2,3-d] pyrimidin-5-yl, 2-amino-4-oxopyrrolo [2.3-d]pyrimidin-3-yl groups, where the purines are attached to the sugar moiety of the oligonucleotides via the 9-position, the pyrimidines via the 1-position, the pyrrolopyridines via the 7-position and the pyrazolopyrimidines via the 1-position.

Structurally, the root oligonucleotide of the ISS-PN component of ISS-PN/IMM is a non-coding sequence which may include at least one unmethylated CpG motif. The relative position of any CpG sequence in ISS-PN with immunostimulatory activity in certain mammalian species (e.g., rodents) is 5'-CG-3' (i.e., the C is in the 5' position with respect to the G in the 3' position). PN/IMM can be conveniently obtained by substituting the cytosine in the CpG dinucleotide with another nucleotide; a particularly useful substitution is with a guanine to form GpG dinucleotide containing PN.

Some oligonucleotide ISS (ISS-ODN) are known. In such ISS-ODN, the CpG motif is flanked by at least two purine nucleotides (e.g., GA or AA) and at least two pyrimidine nucleotides (5'-Purine-Purine-[C]-[G]-Pyrimidine-Pyrimidine-3'). CpG motif-containing ISS-ODN are believed to stimulate B lymphocyte proliferation (see, e.g., Krieg, et al., Nature, 374:546–549, 1995).

The core hexamer structure of the foregoing ISS-PN may be flanked upstream and/or downstream by any number or composition of nucleotides or nucleosides. However, ISS-PN are at least 6 bases in length, and preferably are between 6 and 200 bases in length, to enhance uptake of the ISS-PN/IMM into target tissues. Those of ordinary skill in the art will be familiar with, or can readily identify, reported nucleotide sequences of known ISS-ODN for reference in preparing ISS-PN. For ease of reference in this regard, the following sources are especially helpful:

Yamamoto, et al., *Microbiol.Immunol.*, 36:983 (1992)
Ballas, et al., *J.Immunol.*, 157:1840 (1996)
Klinman, et al., *J.Immunol.*, 158:3635 (1997)
Sato, et al., *Science*, 273:352 (1996)

Each of these articles are incorporated herein by reference for the purpose of illustrating the level of knowledge in the art concerning the nucleotide composition of known ISS-ODN.

In particular, ISS-PN and PN useful in the invention include those which have the following hexameric nucleotide sequences:

1. For ISS-PN, hexamers having "CpG" motifs or, for PN, hexamers having XpY motifs, where X cannot be C if Y is G and vice-versa; and,
2. Inosine and/or uracil substitutions for nucleotides in the foregoing hexamer sequences for use as RNA ISS-ODN.

For example, DNA based ISS-PN useful in the invention include those which have the following hexameric nucleotide sequences:

AACGTT, AGCGTC, GACGTT, GGCGTT, AACGTC, AGCGTC, GACGTC, GGCGTC, AACGCC, AGCGCC, GACGCC, GGCGCC, AGCGCT, GACGCT, GGCGCT, TTCGAA, GGCGTT and AACGCC.

RNA based ISS-PN useful in the invention include those which have the following hexameric nucleotide sequences:

AACGUU, AACGpI, AACGpC, AGCGUC, AGCGpI, AGCGpC, RECEIVED GACGCU, GACGCpI, GACGCpC, GACGUU, GACGpI, GACGPC, GACGUC, GACGpI, GACGpC, and poly (I.C).

The ISS-PN may or may not include palindromic regions. If present, a palindrome may extend only to a CpG motif, if present, in the core hexamer sequence, or may encompass more of the hexamer sequence as well as flanking nucleotide sequences.

In addition, backbone phosphate group modifications (e.g., methylphosphonate, phosphorothioate, phosphoroamidate and phosphorodithioate internucleotide linkages) can confer anti-microbial activity on the ISS-PN and enhance their stability in vivo, making them particularly useful in therapeutic applications. A particularly useful phosphate group modification is the conversion to the phosphorothioate or phosphorodithioate forms of ISS-PN. In addition to their potentially anti-microbial properties, phosphorothioates and phosphorodithioates are more resistant to degradation in vivo than their unmodified oligonucleotide counterparts, making the ISS-PN/IMM of the invention more available to the host.

2. IMM Conjugate Partners

The oligonucleotide base of the ISS-PN/IMM conjugate is conjugated to an IMM which includes an antigen and may further include an immunomodulatory agent. An "antigen" is a substance that is recognized and bound specifically by an antibody or by a T cell antigen receptor. Antigens can include peptides, proteins, glycoproteins and polysaccharides, including portions thereof and combinations thereof. The antigens can be those found in nature or can be synthetic.

The term "inmmunomodulatory" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, CD4+ T lymphocytes, CD8+ T lymphocytes, macrophages and the like; as well as increased synthesis of Th1 associated immunostimulatory cytokines including, but not limited to, IL-6, IL-12, IL-18, IFN-α,β and γ, TNF-α and the like. Immunosuppressive effects include those that directly or indirectly decrease cellular or humoral immune responses.

Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-γ, which can block IL-4 induced class switch to IgE and IgG1, thereby reducing the levels of these antibody subclasses.

Thus, an "immunomodulatory agent" suitable for use as conjugate partners for ISS-PN/IMM can be a peptide, such as an antigen or cytokine. Where the ISS-PN/IMM conjugate partner is a peptide, suitable peptides include purified native peptides, synthetic peptides, recombinant proteins, crude protein extracts, attenuated or inactivated viruses, cells, micro-organisms, or fragments of such peptides.

Protein antigens that can serve as IMM conjugate partners include antigens from a wide variety of sources, including allergens such as plant pollens, dust mite proteins, animal dander, saliva, and fungal spores as well as infectious microorganims. Examples of the latter include attenuated or inactivated viruses such as HIV-1, HIV-2, hepatitis, herpes simplex, rotavirus, polio virus, measles virus, human and bovine papilloma virus, and slow brain viruses. For immunization against tumor formation, the conjugate can include tumor cells (live or irradiated), tumor cell extracts, or protein subunits of tumor antigens. Vaccines for immuno-based contraception can be formed by including sperm proteins as the peptide portion of the conjugate.

Among the suitable cytokines for use as components of IMM conjugate partners are the interleukins (IL-1, IL-2, IL-3, etc.), interferons (e.g., IFN-α, IFN-β, IFN-γ), erythropoietin, colony stimulating factors (e.g., G-CSF, M-CSF, GM-CSF) and TNF-α.

IMN conjugate partners can also include amino acid sequences that mediate protein binding to a specific receptor or that mediate targeting to a specific cell type or tissue. Examples include, but are not limited to, antibodies or antibody fragments; peptide hormones such as human growth hormone; and enzymes. Co-stimulatory molecules such as B7 (CD80), trans-activating proteins such as transcription factors, chemokines such as macrophage chemotactic protein (MCP) and other chemoattractant or chemotactic peptides are also useful peptide-based conjugate partners.

More specifically, suitable antigens for use as ISS-PN/IMM conjugate partners include any molecule capable of being conjugated to an oligonucleotide and eliciting a B cell or T cell antigen-specific response. Preferably, antigens elicit an antibody response specific for the antigen. A wide variety of molecules are antigens. These include, but are not limited to, sugars, lipids, autacoids and hormones, as well as macromolecules such as complex carbohydrates, and phospholipids. Small molecules may need to be haptenized in order to be rendered antigenic.

Preferably the antigens are peptides, polysaccharides (such as the capsular polysaccharides used in *Haemophilus influenza* vaccines), gangliosides and glycoproteins. The antigen may be an intact antigen or T cell epitope(s) of an antigen. These can be obtained through several methods known in the art, including isolation and synthesis using chemical and enzymatic methods. In certain cases, such as for many sterols fatty acids and phospholipids, the antigenic portions are commercially available.

Many antigenic peptides and proteins are known in, and available to the art; others can be identified using conventional techniques. Examples of known antigens include, but are not limited to:

a. Allergens such as reactive major dust mite allergens Der pI and Der pII (see, Chua, et al., *J.Exp.Med.*, 167:175–182, 1988; and, Chua, et al., *Int.Arch.Allergy Appl. Immunol.*, 91:124–129, 1990), T cell epitope peptides of the Der pII allergen (see, Joost van Neerven, et al.,*J.Immunol.*, 151:2326–2335, 1993), the highly abundant Antigen E (Amb aI) ragweed pollen allergen (see, Rafnar, et al., *J.Biol. Chem.*, 266:1229–1236, 1991), phospholipase $A_2$ (bee venom) allergen and T cell epitopes therein (see, Dhillon, et al., *J.Allergy Clin.Immunol.*, :42- , 1992), white birch pollen (Betvl) (see, Breiteneder, et al., *EMBO*, 8:1935–1938, 1989), the Fel dI major domestic cat allergen (see, Rogers, et al., *Mol.Immunol.*, 30:559–568, 1993), tree pollen (see, Elsayed et al., *Scand. J. Clin. Lab. Invest. Suppl.*, 204:17–31, 1991) and grass pollen (see, Malley, *J. Reprod. Immunol.*, 16:173–86, 1989).

b. Live, attenuated and inactivated microorganisms such as inactivated polio virus (Jiang et al., *J. Biol. Stand.*, 14:103–9, 1986), attenuated strains of Hepatitis A virus (Bradley et al., *J. Med. Virol.*, 14:373–86, 1984), attenuated measles virus (James et al., *N. Engl. J. Med.*, 332:1262–6, 1995) and epitopes of pertussis virus (e.g., ACEL-IMUNE® acellular DTP, Wyeth-Lederle Vaccines and Pediatrics).

c. Contraceptive antigens such as human sperm protein (Lea et al., *Biochim. Biophys. Acta*, 1307:263, 1996).

The published sequence data and methods for isolation and synthesis of the antigens described in these articles are incorporated herein by this reference to illustrate knowledge in the art regarding useful antigen sources. Those of ordinary skill in the art will be familiar with, or can readily ascertain, the identity of other useful antigens for use as ISS-PN/IMM conjugate partners.

Particularly useful immunostimulatory peptides for inclusion in IMM are those which stimulate Th1 immune responses, such as IL-12 (Bliss, et al., *J.Immunol.*, 156:887–894, 1996), IL-18, INF-α,β and γ or TGF-α. Conjugation of adjuvants (such as keyhole limpet hemocyanin, KLH) to the ISS-PN/IMM conjugate can further enhance the activity of the ISS-PN/IMM conjugates of the invention.

Other useful adjuvants include cholera toxin, procholeragenoid, cholera toxin B subunit and fungal polysaccharides including, but not limited to, schizophyllan, muramyl dipeptide, muramyl dipeptide derivatives, phorbol esters, microspheres, non-*Helicobacter pylori* bacterial lysates, labile toxin of *Escherichia coli,* block polymers, saponins, and ISCOMs. For additional adjuvants, those of ordinary skill in the art may also refer to, for example, Azuma, I., "Synthetic Immunoadjuvants: Application to Non-Specific Host Stimulation and Potentiation of Vaccine Immunogenicity" *Vaccine*, vol. 10, 1000 (1992); Pockley, A. G. & Montgomery, P. C., "In vivo Adjuvant Effect of Interleukins 5 and 6 on Rat Tear IgA Antibody Responses" *Immunology*, vol. 73, 19–23 (1991); Adam, A. & Lederer, E. "Muramyl peptides as Immunomodulators" *ISI ATLAS OF SCIENCE* 205 (1988); Clements, J. D., et al. "Adjuvant Activity of *Escherichia coli* Heat-labile Enterotoxin and Effect on the Induction of Oral Tolerance in Mice to Unrelated Protein Antigens" *Vaccine*, vol. 6, 269 (1988); Ben Ahmeida, E. T. S., et al. "Immunopotentiation of Local and Systemic Humoral Immune Responses by ISCOMs, Liposomes and FCA: Role in Protection Against Influenza A in Mice" *Vaccine*, vol. 11, 1302 (1993); and Gupta, R. K. et al. "Adjuvants—A Balance Between Toxicity and Adjuvanticity" *Vaccine*, vol. 11, 290–308 (1993).

Those of ordinary skill in the art will appreciate that non-antigen components of IMM described above can also be administered in unconjugated form with an ISS-PN/IMM (antigen only) conjugate. Thus, the co-administration of such components is encompassed by the invention.

C. Synthesis of Polynucleotide Conjugates

1. Polynucleotide Portion

ISS-PN can be synthesized using techniques and nucleic acid synthesis equipment which are well-known in the art. For reference in this regard, see, e.g., Ausubel, et al., *Current Protocols in Molecular Biology*, Chs. 2 and 4 (Wiley Interscience, 1989); Maniatis, et al., *Molecular Cloning: A Laboratory Manual* (Cold Spring Harbor Lab., New York, 1982); U.S. Pat. Nos. 4,458,066 and 4,650,675. When assembled enzymatically, the individual units can be ligated with a ligase such as T4 DNA or RNA ligase as described in, for example, U.S. Pat. No. 5,124,246. Oligonucleotide degradation could be accomplished through the exposure of an oligonucleotide to a nuclease, as exemplified in U.S. Pat.

No. 4,650,675. These references are incorporated herein by reference for the sole purpose of demonstrating knowledge in the art concerning production of synthetic polynucleotides. Because the ISS-PN is non-coding, there is no concern about maintaining an open reading frame during synthesis.

Alternatively, ISS-PN may be isolated from microbial species (especially mycobacteria) using techniques well-known in the art, such as nucleic acid hybridization. Preferably, such isolated ISS-PN will be purified to a substantially pure state; i.e., to be free of endogenous contaminants, such as lipopolysaccharides. ISS-PN isolated as part of a larger polynucleotide can be reduced to the desired length by techniques well known in the art, such as by endonuclease digestion. Those of ordinary skill in the art will be familiar with, or can readily ascertain, techniques suitable for isolation, purification and digestion of polynucleotides to obtain ISS-PN of potential use in the invention.

Circular ISS-PN can be isolated, synthesized through recombinant methods, or chemically synthesized. Where the circular ISS-PN is obtained through isolation or through recombinant methods, the ISS-PN will preferably be a plasmid. The chemical synthesis of smaller circular oligonucleotides can be performed using literature methods (Gao et al., Nucleic Acids Res. (1995) 23:2025–9; Wang et al., Nucleic Acids Res. (1994) 22:2326–33).

The ISS-PN can also contain modified oligonucleotides. These modified oligonucleotides can be synthesized using standard chemical transformations. The efficient solid-support based construction of methylphosphonates has been described. Agrawal et al. (19) Tet. Lett. 28:3539–3542. The synthesis of other phosphorous based modified oligonucleotides, such as phosphotriesters (Miller et al. JACS 93, 6657–6665), phosphoramidates (Jager et al, Biochemistry 27, 7247–7246), and phosphorodithioates (U.S. Pat. No. 5,453,496) has also been described. Other non-phosphorous based modified oligonucleotides can also be used (Stirchak et al., Nucleic Acids Res. 17, 6129–6141).

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also bee described (e.g., U.S. Pat. Nos. 4,849,513, 5,015,733, 5,118,800, 5,118,802) and can be used similarly.

The techniques for making phosphate group modifications to oligonucleotides are known in the art and do not require detailed explanation. For review of one such useful technique, the an intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phophorothioates. The same general technique (excepting the sulfur treatment step) can be applied to yield methylphosphoamidites from methylphosphonates. For more details concerning phosphate group modification techniques, those of ordinary skill in the art may wish to consult U.S. Pat. Nos. 4,425,732; 4,458,066; 5,218,103 and 5,453,496, as well as Tetrahedron Lett. at 21:4149 (1995), 7:5575 (1986), 25:1437 (1984) and Journal Am. ChemSoc., 93:6657 (1987), the disclosures of which are incorporated herein for the sole purpose of illustrating the standard level of knowledge in the art concerning preparation of these compounds.

2. Linking the PN Component to the IMM Component

The ISS-PN component can be linked to the IMM portion of the conjugate in a variety of ways. The link can be made at the 3' or 5' end of the ISS-PN, or to a suitably modified base at an internal position in the PN. If the peptide contains a suitable reactive group (e.g., an N-hydroxysuccinimide ester) it can be reacted directly with the $N^4$ amino group of cytosine residues. Depending on the number and location of cytosine residues in the ISS-PN, specific labeling at one or more residues can be achieved.

Alternatively, modified oligonucleosides, such as are known in the art, can be incorporated at either terminus, or at internal positions in the ISS-PN. These can contain blocked functional groups which, when deblocked, are reactive with a variety of functional groups which can be present on, or attached to, a peptide of interest.

The IMM portion of the conjugate can be attached to the 3'-end of the ISS-PN through solid support chemistry. For example, the ISS-PN portion can be added to a polypeptide portion that has been pre-synthesized on a support (Haralambidis et al., Nucleic Acids Res. (1990) 18:493–99; Haralambidis et al., Nucleic Acids Res. (1990) 18:501–505). Alternatively, the PN can be synthesized such that it is connected to a solid support through a cleavable linker extending from the 3'-end. Upon chemical cleavage of the ISS-PN from the support, a terminal thiol group is left at the 3'-end of the ISS-PN (Zuckermann et al., Nucleic Acids Res. (1987) 15:5305–5321; Corey et al., (1987) Science 238:1401–1403), or a terminal amine group is left at the 3'-end of the PN (Nelson et al., Nucleic Acids Res. (1989) 17:1781–94). Conjugation of the amino-modified PN to amino groups of the peptide can be performed as described in Benoit et al., Neuromethods (1987) 6:43–72. Conjugation of the thiol-modified ISS-PN to carboxyl groups of the peptide can be performed as described in Sinah et al., Oligonucleotide Analogues: A Practical Approach (1991) IRL Press.

The IMM portion of the conjugate can be attached to the 5'-end of the ISS-PN through an amine, thiol, or carboxyl group that has been incorporated into the ISS-PN during its synthesis. Preferably, while the ISS-PN is fixed to the solid support, a linking group comprising a protected amine, thiol, or carboxyl at one end, and a phosphoramidite at the other, is covalently attached to the 5'-hydroxyl (Agrawal et al., Nucleic Acids Res. (1986) 14:6227–6245; Connolly, Nucleic Acids Res. (1985) 13:4485–4502; Coull et al., Tetrahedron Lett. (1986) 27:3991–3994; Kremsky et al., Nucleic Acids Res. (1987) 15:2891–2909; Connolly, Nucleic Acids Res. (1987) 15:3131–3139; Bischoff et al., Anal. Biochem. (1987) 164:336–344; Blanks et al., Nucleic. Acids Res. (1988) 16:10283–10299; U.S. Pat. Nos. 4,849, 513, 5,015,733, 5,118,800, and 5,118,802). Subsequent to deprotection, the latent amine, thiol, and carboxyl functionalities can be used to covalently attach the PN to a peptide (Benoit et al., Neuromethods (1987) 6:43–72; Sinah et al., Oligonucleotide Analogues: A Practical Approach (1991) IRL Press).

A peptide portion can be attached to a modified cytosine or uracil at any position in the ISS-PN. The incorporation of a "linker arm" possessing a latent reactive functionality, such as an amine or carboxyl group, at C-5 of the modified base provides a handle for the peptide linkage (Ruth, 4th Annual Congress for Recombinant DNA Research, p. 123).

The linkage of the ISS-PN to a peptide can also be formed through a high-affinity, non-covalent interaction such as a biotin-streptavidin complex. A biotinyl group can be attached, for example, to a modified base of an oligonucleotide (Roget et al., Nucleic Acids Res. (1989) 17:7643–7651). Incorporation of a streptavidin moiety into the peptide portion allows formation of a non-covalently bound complex of the streptavidin conjugated peptide and the biotinylated PN.

The linkage of the ISS-PN to a lipid can be formed using standard methods. These methods include, but are not limited to, the synthesis of oligonucleotide-phospholipid conjugates (Yanagawa et al., Nucleic Acids Symp. Ser. (1988) 19:189–92), oligonucleotide-fatty acid conjugates (Grabarek et al., Anal. Biochem. (1990) 185:131–35; Staros et al., Anal. Biochem. (1986) 156:220–22), and oligonucleotide-sterol conjugates (Boujrad et al., Proc. Natl. Acad. Sci. USA (1993) 90:5728–31).

The linkage of the ISS-PN to a oligosaccharide can be formed using standard known methods. These methods include, but are not limited to, the synthesis of oligonucleotide-oligosaccharide conjugates, wherein the oligosaccharide is a moiety of an immunoglobulin (O'Shannessy et al., J. Applied Biochem. (1985) 7:347–55).

Adjuvants and cytokines may also be genetically or chemically linked to the ISS-ODN conjugates. Examples of this type of fusion peptide are known to those skilled in the art and can also be found in Czerkinsky et al., *Infect. Immun.*, 57: 1072–77 (1989); Nashar et al., *Vaccine,* 11: 235–40 (1993); and Dertzbaugh and Elson, *Infect. Immun.,* 61: 48–55 (1993).

The linkage of a circular ISS-PN to an IMM can be formed in several ways. Where the circular PN is synthesized using recombinant or chemical methods, a modified nucleoside (Ruth, in *Oligonucleotides and Analogues: A Practical Approach* (1991) IRL Press). Standard linking technology can then be used to connect the circular ISS-PN to the antigen or immunostimulatory peptide (Goodchild, Bioconjugate Chem. (1990) 1:165). Where the circular ISS-PN is isolated, or synthesized using recombinant or chemical methods, the linkage can be formed by chemically activating, or photoactivating, a reactive group (e.g. carbene, radical) that has been incorporated into the antigen or immunostimulatory peptide.

Additional methods for the attachment of peptides and other molecules to ISS-PNs can be found in C. Kessler: *Nonradioactive labeling methods for nucleic acids* in L. J. Kricka (ed.) "Nonisotopic DNA Probe Techniques," Academic Press 1992 and in Geoghegan and Stroh, *Bioconjug. Chem.*, 3:138–146, 1992.

D. Methods and Routes for Administration of ISS-PN/IMM to a Host

1. Drug Delivery

The ISS-PN/IMM of the invention are administered to a host using any available method and route suitable for drug delivery, including ex vivo methods (e.g., delivery of cells incubated or transfected with an ISS-PN/IMM) as well as systemic or localized routes. However, those of ordinary skill in the art will appreciate that methods and localized routes which direct the ISS-PN/IMM into antigen-sensitized tissue will be preferred in most circumstances to systemic routes of administration, both for immediacy of therapeutic effect and avoidance of in vivo degradation.

The entrance point for many exogenous antigens into a host is through the skin or mucosa. Thus, delivery methods and routes which target the skin (e.g., for cutaneous and subcutaneous conditions) or mucosa (e.g., for respiratory, ocular, lingual or genital conditions) will be especially useful. Those of ordinary skill in the clinical arts will be familiar with, or can readily ascertain, means for drug delivery into skin and mucosa. For review, however, exemplary methods and routes of drug delivery useful in the invention are briefly discussed below.

Intranasal administration means are particularly useful in addressing respiratory inflammation, particularly inflammation mediated by antigens transmitted from the nasal passages into the trachea or broncheoli. Such means include inhalation of aerosol suspensions or insufflation of the polynucleotide compositions of the invention. Nebulizer devices suitable for delivery of polynucleotide compositions to the nasal mucosa, trachea and bronchioli are well-known in the art and will therefore not be described in detail here. For general review in regard to intranasal drug delivery, those of ordinary skill in the art may wish to consult Chien, *Novel Drug Delivery Systems,* Ch. 5 (Marcel Dekker, 1992).

Dermal routes of administration, as well as subcutaneous injections, are useful in addressing allergic reactions and inflammation in the skin. Examples of means for delivering drugs to the skin are topical application of a suitable pharmaceutical preparation, transdermal transmission, injection and epidermal administration.

For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. An exemplary device for use in epidermal administration employs a multiplicity of very narrow diameter, short tynes which can be used to scratch ISS-PN/IMM coated onto the tynes into the skin. The device included in the MONO-VACC old tuberculin test manufactured by Pasteur Merieux of Lyon, France is suitable for use in epidermal administration of ISS-PN/IMM. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Opthalmic administration (e.g., for treatment of allergic conjunctivitis) involves invasive or topical application of a pharmaceutical preparation to the eye. Eye drops, topical cremes and injectable liquids are all examples of suitable mileaus for delivering drugs to the eye.

Systemic administration involves invasive or systemically absorbed topical administration of pharamaceutical preparations. Topical applications as well as intravenous and intramuscular injections are examples of common means for systemic administration of drugs.

2. Dosing Parameters

A particular advantage of the ISS-PN/IMM of the invention is their capacity to exert immunomodulatory activity even at relatively minute dosages. Although the dosage used will vary depending on the clinical goals to be achieved, a suitable dosage range is one which provides up to about 1–1000 μg of ISS-PN/IMM/ml of carrier in a single dosage. Alternatively, a target dosage of ISS-PN/IMM can be considered to be about 1–10 μM in a sample of host blood drawn within the first 24–48 hours after administration of ISS-PN/IMM. Based on current studies, ISS-PN/IMM are believed to have little or no toxicity at these dosage levels.

In this respect, it should be noted that the anti-inflammatory and immunotherapeutic activity of ISS-PN/IMM in the invention is essentially dose-dependent. Therefore, to increase ISS-PN/IMM potency by a magnitude of two, each single dose is doubled in concentration. Clinically, it may be advisable to administer the ISS-PN/IMM in a low dosage (e.g., about 1 μg/ml to about 50 μg/ml), then increase the dosage as needed to achieve the desired therapeutic goal.

In view of the teaching provided by this disclosure, those of ordinary skill in the clinical arts will be familiar with, or can readily ascertain, suitable parameters for administration of ISS-PN/IMM according to the invention.

3. ISS-PN/lMM Compositions

ISS-PN/IMM will be prepared in a pharmaceutically acceptable composition for delivery to a host. Pharmaceutically acceptable carriers preferred for use with the ISS-PN/IMM of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A composition of ISS-PN/IMM may also be lyophilized using means well known in the art, for subsequent reconstitution and use according to the invention.

Absorption promoters, detergents and chemical irritants (e.g., keritinolytic agents) can enhance transmission of an ISS-PN/IMM composition into a target tissue. For reference concerning general principles regarding absorption promoters and detergents which have been used with success in mucosal delivery of organic and peptide-based drugs, see Chien, *Novel Drug Delivery Systems*, Ch. 4 (Marcel Dekker, 1992).

Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from Regular Solution Theory to Describe Partitioning-Driven Processes*, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the ISS-PN/IMM to specific tissue. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., *Nuc.Acids Symp.Ser.,* 19:189 (1988); Grabarek, et al., *Anal.Biochem.,* 185:131 (1990); Staros, et al., *Anal.Biochem.,* 156:220 (1986) and Boujrad, et al., *Proc.Natl.Acad.Sci.USA,* 90:5728 (1993), the disclosures of which are incorporated herein by reference solely to illustrate the standard level of knowledge in the art concerning conjugation of PNs to lipids). Targeted delivery of ISS-PN/IMM can also be achieved by conjugation of the ISS-PN/IMM to a the surface of viral and non-viral recombinant expression vectors, to an antigen or other ligand, to a monoclonal antibody or to any molecule which has the desired binding specificity.

Co-administration of a peptide drug with an ISS-PN/IMM according to the invention may also be achieved by incorporating the ISS-PN/IMM in cis or in trans into a recombinant expression vector (plasmid, cosmid, virus or retrovirus) which codes for any therapeutically beneficial protein deliverable by a recombinant expression vector. If incorporation of an ISS-PN/IMM into an expression vector for use in practicing the invention is desired, such incorporation may be accomplished using conventional techniques which do not require detailed explanation to one of ordinary skill in the art. For review, however, those of ordinary skill may wish to consult Ausubel, *Current Protocols in Molecular Biology,* supra.

D. Screening for Active ISS-PN/IMM

Confirmation that a particular compound has the properties of an ISS-PN/IMM useful in the invention can be obtained by evaluating whether the ISS-PN/IMM affects cytokine secretion and IgG antibody isotype production as described in Section A.I, above. Details of in vitro techniques useful in making such an evaluation are given in the Examples; those of ordinary skill in the art will also know of, or can readily ascertain, other methods for measuring cytokine secretion and antibody production along the parameters taught herein.

E. Kits for Use in Practicing the Methods of the Invention

For use in the methods described above, kits are also provided by the invention. Such kits may include any or all of the following: ISS-PN/IMM (conjugated or unconjugated); a pharmaceutically acceptable carrier (may be pre-mixed with the ISS-PN/IMM) or suspension base for reconstituting lyophilized ISS-PN/IMM; additional medicaments; a sterile vial for each ISS-PN/IMM and additional medicament, or a single vial for mixtures thereof; device(s) for use in delivering ISS-PN/IM to a host; assay reagents for detecting indicia that the anti-inflammatory and/or immunostimulatory effects sought have been achieved in treated animals and a suitable assay device.

Examples illustrating the practice of the invention are set forth below. The examples are for purposes of reference only and should not be construed to limit the invention, which is defined by the appended claims. All abbreviations and terms used in the examples have their expected and ordinary meaning unless otherwise specified.

EXAMPLE I

Selective Induction of a Th1 Response in a Host After Administration of an ISS-PN/IMM In mice, IgG 2A antibodies are serological markers for a Th1 type immune response, whereas IgG 1 antibodies are indicative of a Th2 type immune response. Th2 responses include the allergy-associated IgE antibody class; soluble protein antigens tend to stimulate relatively strong Th2 responses. In contrast, Th1 responses are induced by antigen binding to macrophages and dendritic cells.

To determine which response, if any, would be produced by mice who received ISS-PN/IMM according to the invention, eight groups of Balb/c mice were immunized with 10 μg β-galactosidase protein (conjugated to avidin; Sigma, St. Louis, Mo.) to produce a model allergic phenotype. As set forth in the Table below, some of the mice received antigen alone, some received an antigen-ISS-PN conjugate or a conjugate using a mutant, non-stimulatory PN as a conjugate for the antigen, and others received the antigen in an unconjugated mixture with an ISS-PN. Naive mice are shown for reference:

| Mouse Group | ISS-PN/IMM Treatment |
| --- | --- |
| 1 | None (β-gal antigen vaccinated) |
| 2 | DY1018-βgal conjugate (ISS-PN/IMM) |
| 3 | DY1019-βgal conjugate (PN/IMM) |
| 4 | DY1018 mixed with βgal (unconjugated) |
| 5 | βgal in adjuvant (almn) |
| 6 | plasmid DNA (ISS-ODN present but not expressible with antigen) |
| 7 | naive mice (no antigen priming) |

DY1018 has the nucleotide sequence:
5'-TGACTGTGAACGTTCGAGATGA-3' with a phosphothioate backbone (SEQ ID NO:1) and
DY1019 has the nucleotide sequence:
5'-TGACTGTGAAGGTTGGAGATGA-3' with a phosphothioate backbone (SEQ ID NO:2).

At 2 week intervals, any IgG 2a and IgG 1 to β-galactosidase present in the serum of each mouse were measured by enzyme-linked immunoabsorbent assay (using antibodies specific for the IgG 1 and IgG 2A subclasses) on microtiter plates coated enzyme.

Figure 2:
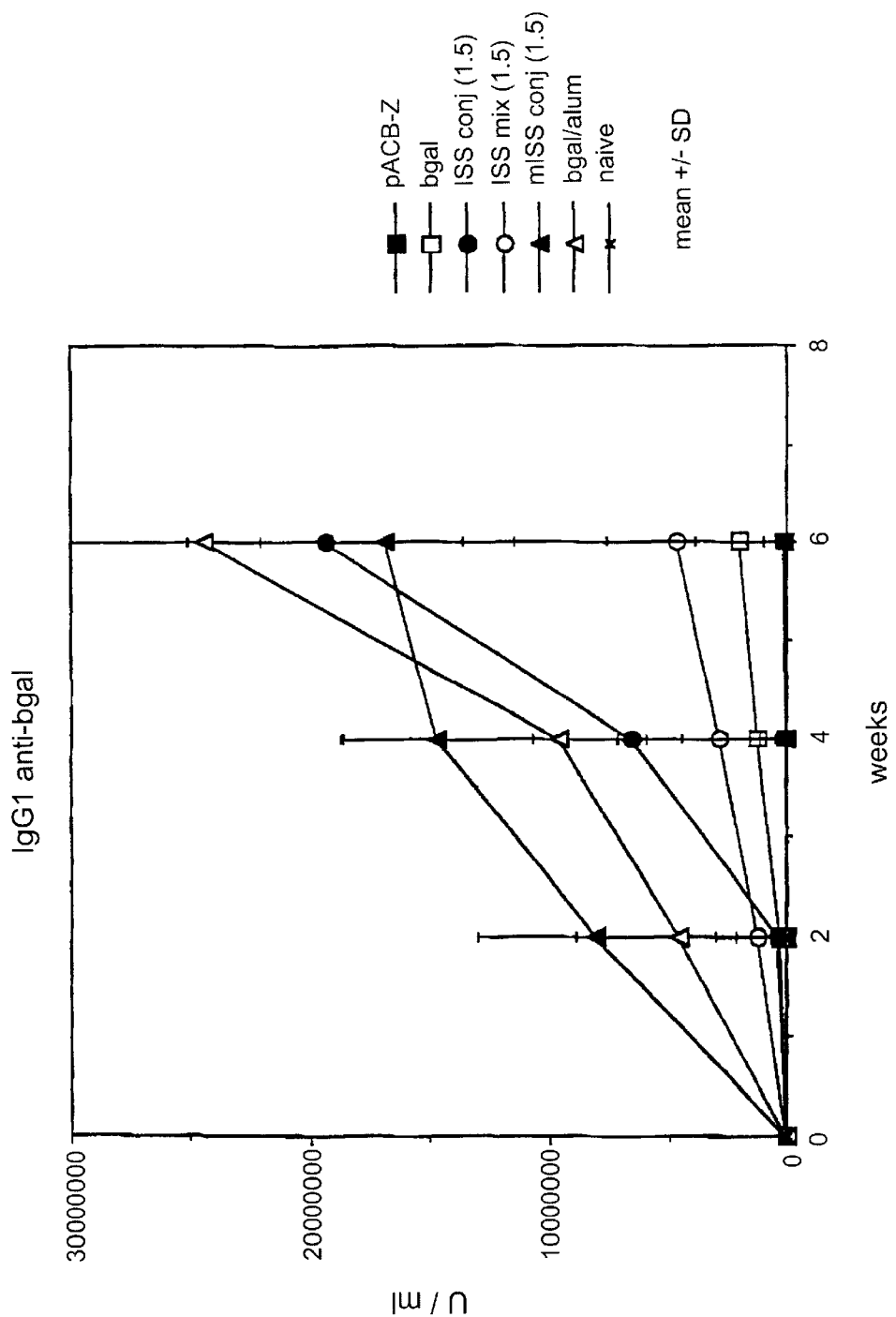
FIG. 2 is a graph of data demonstrating the levels of Th2-type immune responses (as measured by production of IgG1 against an IMM antigen) stimulated by an ISS containing, antigen encoding plasmid (pACB-Z); the antigen alone (β-gal); the antigen mixed with an ISS (1:5 ratio); the antigen conjugated to a non-stimulatory PN (mISS conj; 1:5 ratio); the antigen in adjuvant (alum) and, for reference, the IgG1 levels in naive (unexposed) mice, all as compared to the vigorous Th1-type immune response produced in mice immunized with ISS-PN/IMM (1:5 ratio). The horizontal axis represents the levels (units/ml) of antibody; the vertical axis represents the number of weeks following primary antigen exposure.

As shown in FIG. 1, only the mice who received the ISS-PN/IMM produced high titers of IgG 2A antibodies, which increased in number over a period of 8 weeks. As shown in FIG. 2, immunization of the mice with the antigen itself or with the PN/IMM induced production of relatively high titers of IgG 1 antibodies. The data shown in the FIGURES comprise averages of the values obtained from each group of mice.

To evaluate the effect of treatment of a host before and after a secondary antigen challenge, 3 groups of Balb/c mice were immunized with 10 μg of antigen E (AgE) in alum to produce a model allergic phenotype and challenged again with the antigen, ISS-PN/IMM or mutant (nonstimulatory) PN/IMM at 5 weeks post-priming. An ELISA for IgG1 and IgG2a antibodies was performed as described 4 weeks after priming (one week before secondary antigen challenge) and again at 7 weeks (2 weeks after secondary challenge).

Figure 3:
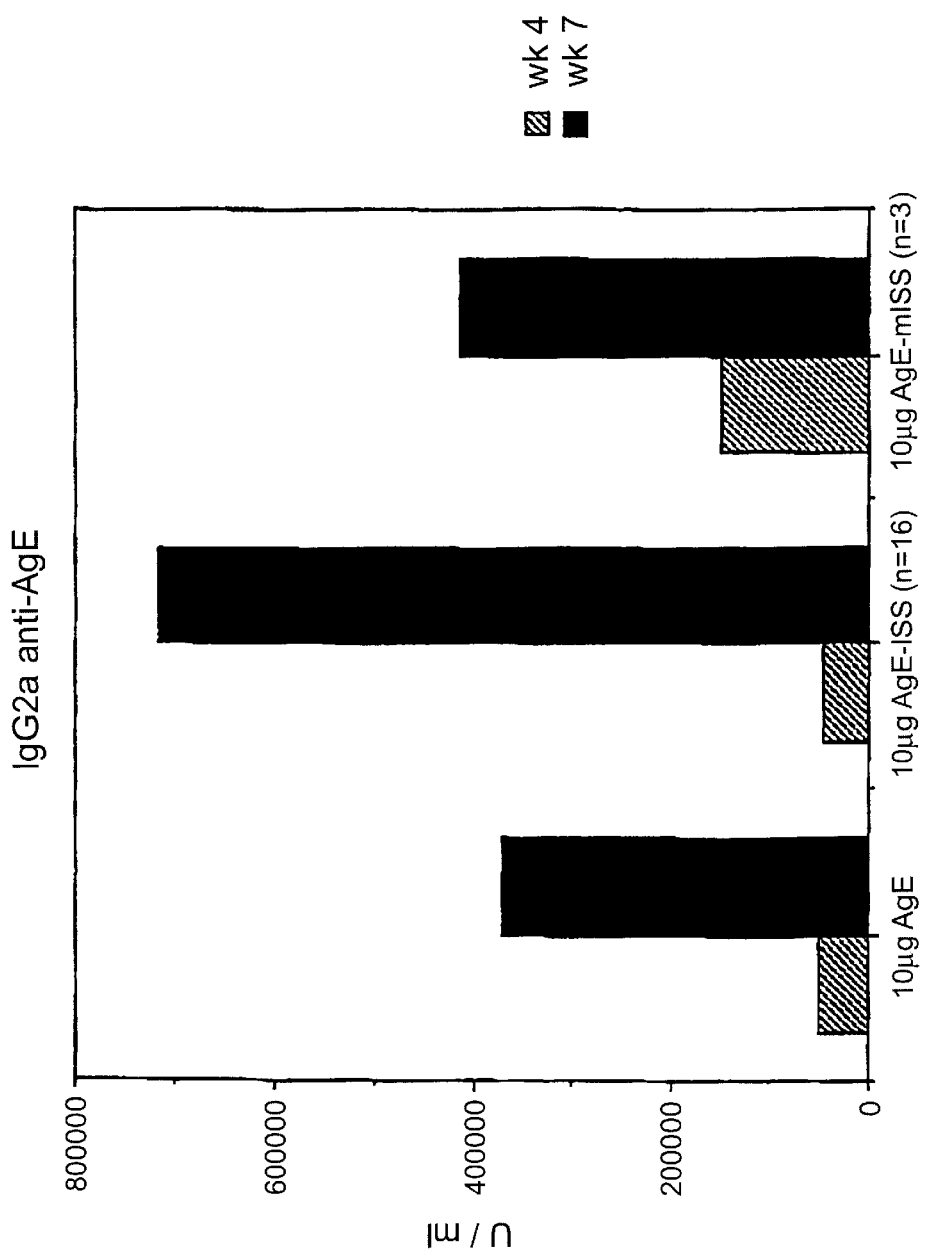
FIG. 3 is a graph of data demonstrating the vigorous Th1-type immune response (as measured by production of IgG2a against an IMM antigen) stimulated by ISS-PN/IMM in comparison to the levels of Th2-like responses stimulated by the antigen alone (AgE) and antigen conjugated to a non-stimulatory PN (mISS conj). Antigen to PN ratios are all 1:5. The horizontal axis represents the levels (units/ml) of antibody; the vertical axis shows the levels at 4 weeks following primary antigen exposure (shaded bars) and at 2 weeks following secondary antigen challenge (solid bars).
Figure 4:
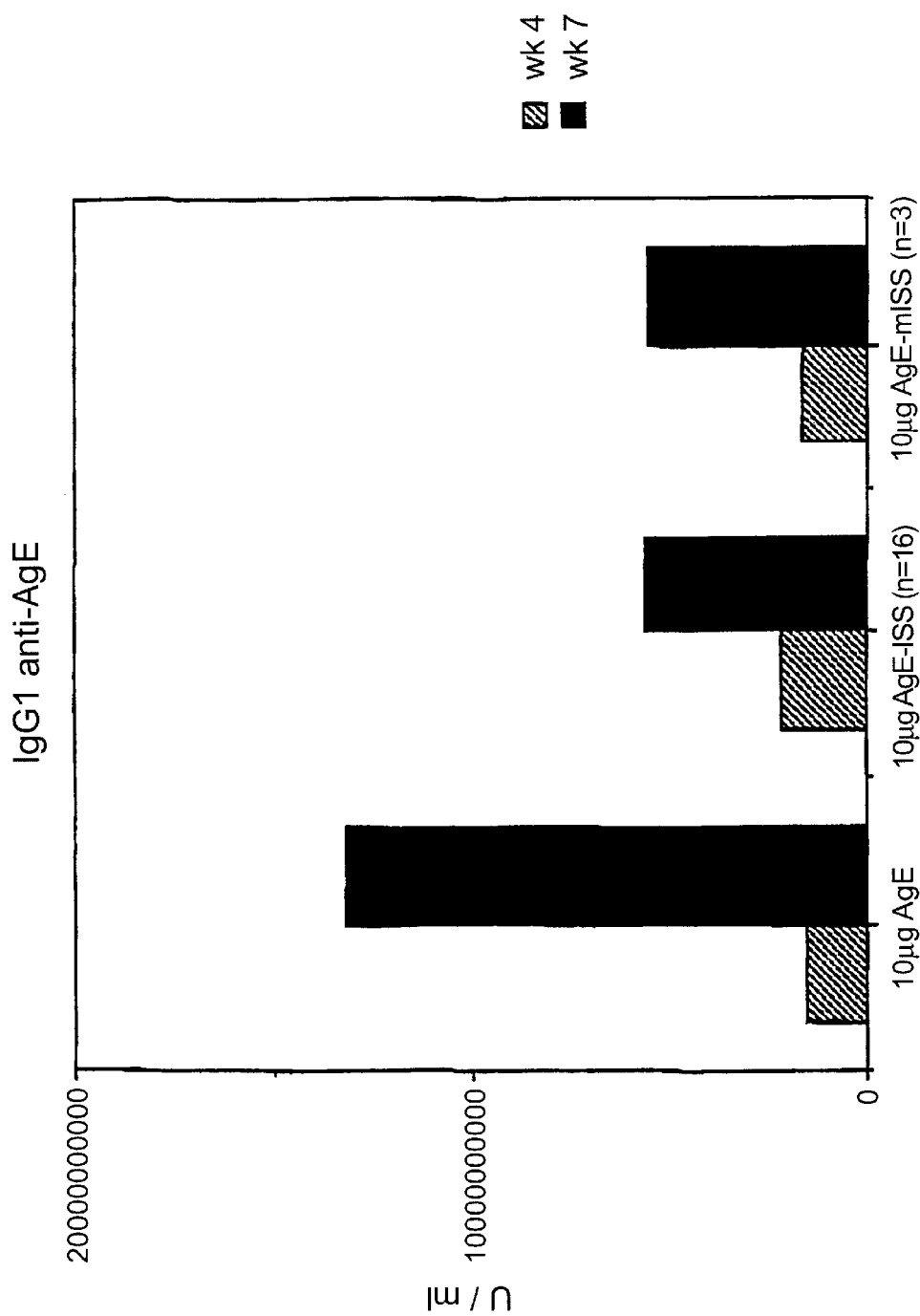
FIG. 4 is a graph of data demonstrating the levels of Th2-type immune responses (as measured by production of IgG1 against an IMM antigen) stimulated by the antigen alone (AgE) and antigen conjugated to a non-stimulatory PN (mISS conj) in comparison to the vigorous Th1-type immune response stimulated in ISS-PN/IMM immunized mice. Antigen to PN ratios are all 1:5. The horizontal axis represents the levels (units/ml) of antibody; the vertical axis shows the levels at 4 weeks following primary antigen exposure (shaded bars) and at 2 weeks following secondary antigen challenge (solid bars).

Again, the mice who received the ISS-PN/IMM mounted a strong Th1 type response to the antigen (IMM) as compared to the antigen-immunized and mutant PN/IMM immunized mice (FIG. 3), while the reverse was true of a Th2 type response in the same mice (FIG. 4).

These data indicate that a selective Th1 response is induced by administration of an ISS-PN/IMM according to the invention to both an antigen-primed (pre-antigen challenge) and an antigen-challenged host.

EXAMPLE II

Suppression of IgE Antibody Response to Antigen by Immunization With ISS-PN/IMM

To demonstrate the IgE suppression achieved through stimulation of a Th1 type cellular immune response in preference to a Th2 type cellular immune response, five to eight week old Balb/c mice were immnunized with AgE as described in the previous Example.

IgE anti-Age were detected using a solid phase radioimmunoassay (RAST) in a 96 well polyvinyl plate (a radioisotopic modification of the ELISA procedure described in Coligan, "*Current Protocols In Immunology*", Unit 7.12.4, Vol. 1, Wiley & Sons, 1994), except that purified polyclonal goat antibodies specific for mouse $\epsilon$ chains were used in lieu of antibodies specific for human Fab. To detect anti-AgE IgE, the plates were coated with AgE (10 μg/ml). The lowest IgE concentration measurable by the assay employed was 0.4 ng of IgE/ml.

Figure 5:
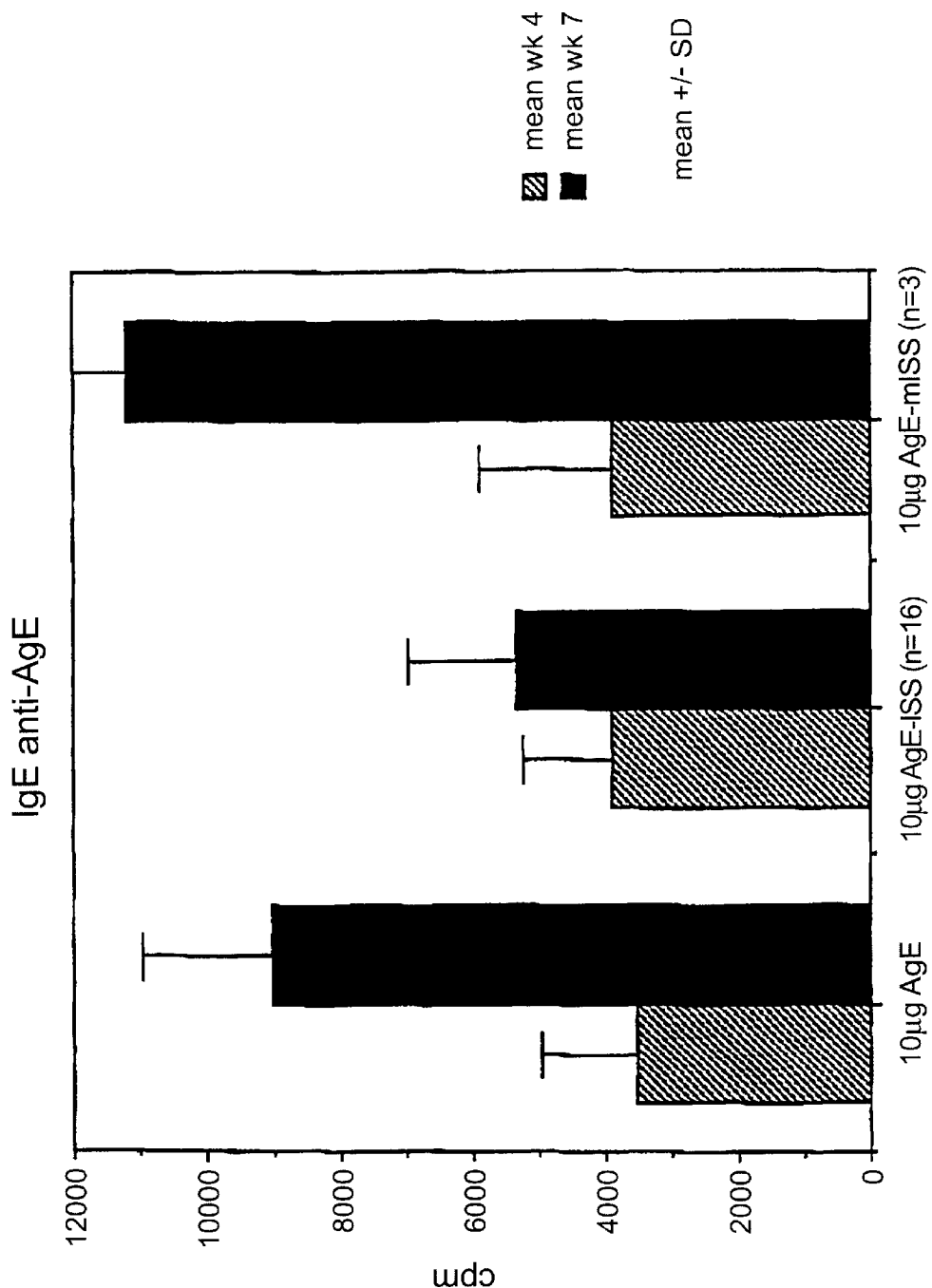
FIG. 5 is a graph of data demonstrating suppression of Th2 associated anti-antigen (AgE) IgE production by ISS-PN/IMM in comparison to the levels of IgE production stimulated by the antigen alone (AgE) and the antigen conjugated to a non-stimulatory PN (mISS conj). Antigen to PN ratios are all 1:5. The horizontal axis represents the levels (counts per minute; cpm) of antibody; the vertical axis shows the levels at 4 weeks following primary antigen exposure (shaded bars) and at 2 weeks following secondary antigen challenge (solid bars).

Measuring specifically the anti-antigen response by each group of mice, as shown in FIG. 5, anti-AgE IgE levels in the ISS-PN/IMM immunized mice were consistently low both before and after boosting, while the protein and mutant ISS-PN/IMM injected mice developed high levels of anti-AgE after antigen challenge.

These data show that the ISS-PN/IMM immunized mice developed an antigen specific Th1 response (suppressing the Th2 IgE response) to the antigen.

EXAMPLE III

INFγ Levels in Mice After Delivery of ISS-PN/IMM

BALB/c mice were immunized with βgal as described in Example I then sacrificed 24 hrs later. Splenocytes were harvested from each mouse.

96 well microtiter plates were coated with anti-CD3 antibody (Pharmingen, La Jolla, Calif.) at a concentration of 1 μg/ml of saline. The anti-CD3 antibody stimulates T cells by delivering a chemical signal which mimicks the effects of binding to the T cell receptor (TCR) complex. The plates were washed and splenocytes added to each well (4×105/well) in a medium of RPMI 1640 with 10% fetal calf serum. Supernatants were obtained at days 1, 2 and 3.

Th1 cytokine (INFγ) levels were assayed with an anti-INFγ murine antibody assay (see, e.g., Coligan, "*Current Protocols in Immunology*", Unit 6.9.5., Vol. 1, Wiley & Sons, 1994). Relatively low levels of INF-γ would be expected in mice with a Th2 phenotype, while relatively high levels of INF-γ would be expected in mice with a Th1 phenotype.

As shown in FIG. 5, levels of Th1 stimulated IFN-γ secretion were greatly increased in the ISS-PN/IMM treated mice, but substantially reduced in each other set of mice (as compared to the control), indicating development of a Th2-type phenotype in the latter mice and a Th1 phenotype in the ISS-PN/IMM treated mice.

EXAMPLE IV

Boosting of CTL Responses by ISS-PN/IMM

Figure 6:
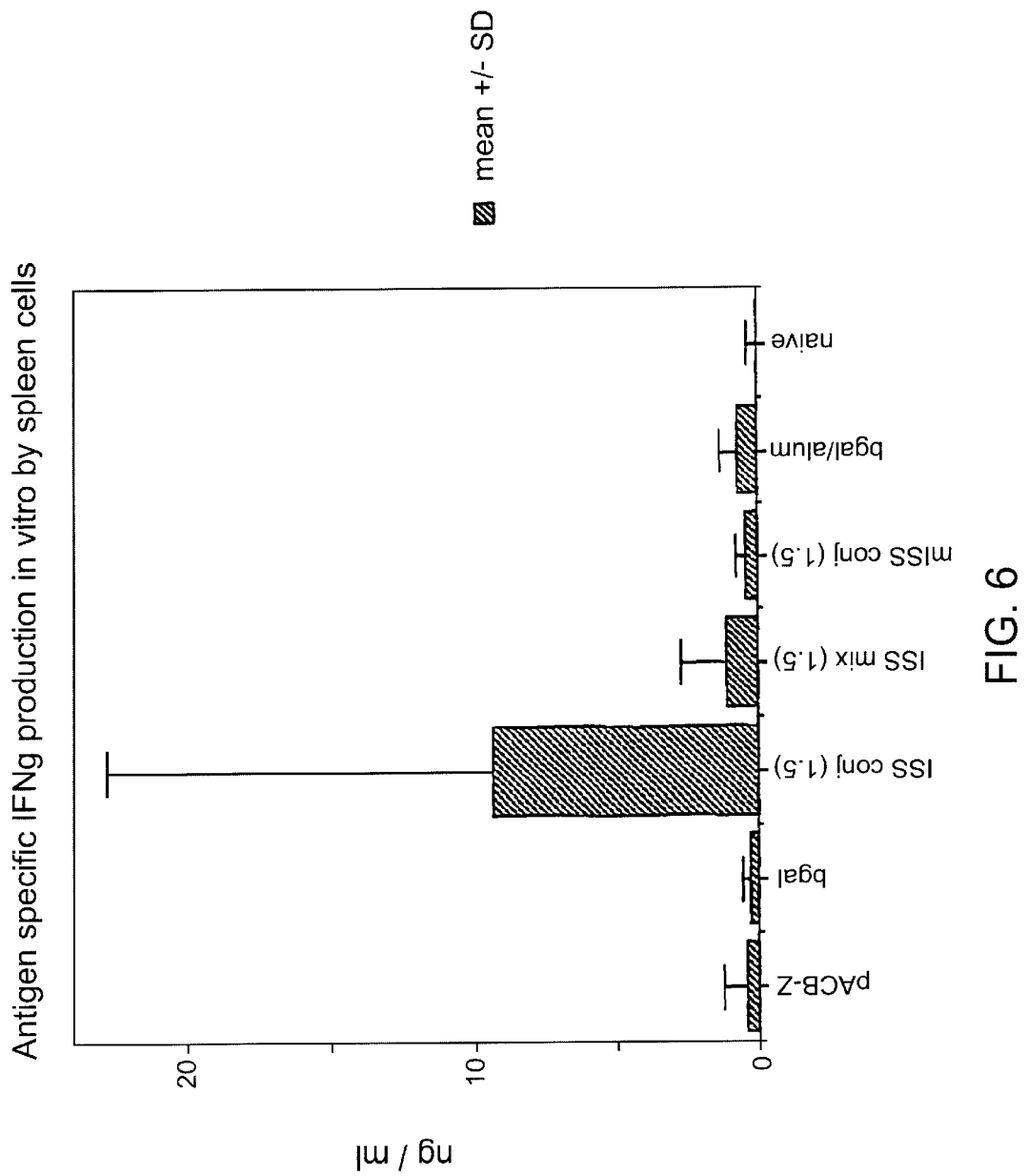
FIG. 6 is a graph of data demonstrating the high levels of Th1 associated interferon γ (IFNg) production stimulated by ISS-PN/IMM in comparison to the relatively low levels of the Th1 cytokine stimulated by an ISS containing, antigen encoding plasmid (pACB-Z); the antigen alone (β-gal); the antigen mixed with an ISS; the antigen conjugated to a non-stimulatory PN (mISS conj); the antigen in adjuvant (alum) and, for reference, the IFNg levels in naive (unexposed) mice. Antigen to PN ratios are all 1:5. The horizontal axis represents the levels (ng/ml) of cytokine; the vertical axis shows the levels of cytokine at 4 weeks following primary antigen exposure (shaded bars).
Figure 7:
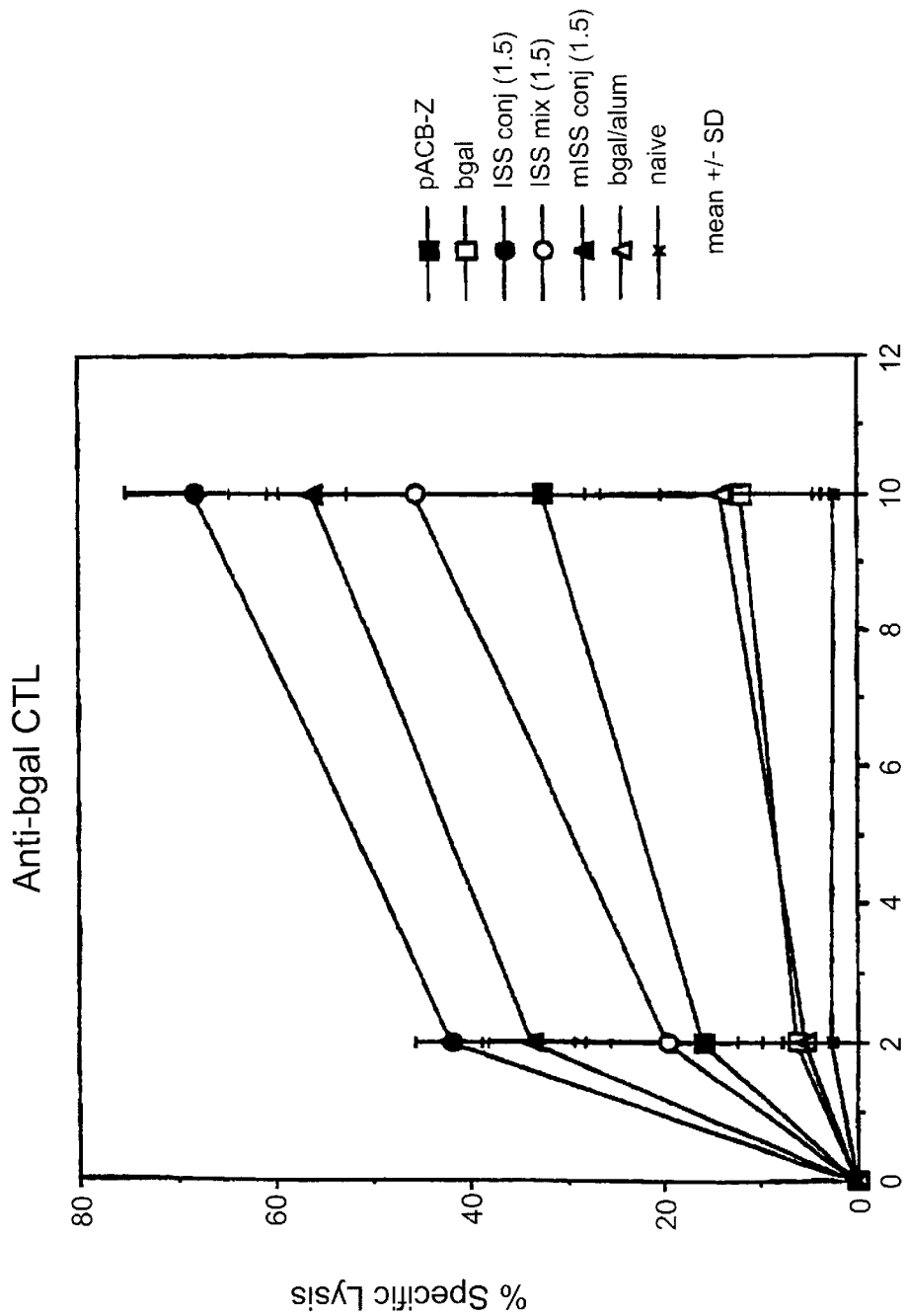
FIG. 7 is a graph of data demonstrating the vigorous antigen-specific cytotoxic T lymphocyte (CTL) response stimulated by ISS-PN/IMM in comparison to the levels of CTL production stimulated by an ISS containing, antigen encoding plasmid (pACB-Z; the antigen alone (β-gal); the antigen mixed with an ISS; the antigen conjugated to a non-stimulatory PN (mISS conj); the antigen in adjuvant (alum) and, for reference, the CTL levels in naive (unexposed) mice. Antigen to PN ratios are all 1:5. The horizontal axis represents the levels of antigen-specific cell lysis obtained (as a percentage of control; no antigen); the vertical axis shows the levels of CTL detected at different effector (antigen) to target ratios, from 0:1 to 10:1. The legend identifies how each cell population was treated.

A mixture of lymphoytes was obtained and contacted with βgal antigen alone or as part of the constructs and mixtures described in Example I. As shown in FIG. 6, CTL production in response to ISS-PN/IMM was consistently higher than the response to antigen delivered in other forms; even twice as high than in animals treated with an unconjugated mixture of ISS-PN and IMM antigen.

In the experiment, the higher values for the mice treated with M-ISS-PN/IMM after antigen challenge as compared to the conventionally immunized mice is most likely owing to the antigen carrier properties of DY1019.

Thus, longer-term immunity mediated by cellular immune responses is benefitted by treatment according to the invention.

What is claimed is:

1. An immunomodulatory composition comprising an immunomodulatory molecule, wherein said immunomodulatory molecule comprises an antigen, wherein the antigen is conjugated to an immunostimulatory polynucleotide (ISS-PN), said ISS-PN comprising an immunostimulatory sequence (ISS) comprising the sequence 5'-cytosine, guanine-3', wherein the ISS is at least six nucleotides in length, wherein said ISS-PN is from 6 to about 200 nucleotides in length, and wherein the antigen is selected from a tumor antigen, a viral antigen, and an allergen.

2. The composition of claim 1, wherein the ISS comprises the sequence 5'-Purine, Purine, C, G, Pyrimidine, Pyrimidine-3'.

3. The composition of claim 2, wherein at least one Pyrimidine is uracil.

4. The composition of claim 2, wherein the ISS comprises a sequence selected from the group consisting of AACGTT, AGCGTT, GACGTT, GGCGTT, AACGTC, AGCGTC, GACGTC, GGCGTC, AACGCC, AGCGCC, GACGCC, GGCGCC, AACGCT, AGCGCT, GACGCT, and GGCGCT.

5. The composition of claim 2, wherein the ISS comprises a sequence selected from the group consisting of AACGTT, AGCGTT, GACGTT, GGCGTT, AACGTC, and AGCGTC.

6. The composition of claim 2, wherein the ISS comprises a sequence selected from the group consisting of AACGTT, AGCGTT, and GACGTT.

7. The composition of claim 2, wherein the ISS comprises the sequence TGACTGTGAACGTTCGAGATGA (SEQ ID NO:1).

8. The composition of claim 2, wherein the ISS comprises a sequence selected from the group consisting of AACGTU, AACGUT, AACGUU, AGCGTU, AGCGUT, AGCGUU, GACGUT, GACGTU, GACGUU, GGCGTU, GGCGUT, GGCGUU, AACGUC, AGCGUC, GACGUC, GGCGUC, AACGCU, AGCGCU, GACGCU, and GGCGCU.

9. The composition of claim 2, wherein the ISS comprises AACGUT.

10. The composition of claim 1, wherein the polynucleotide further comprises a phosphate backbone modification.

11. The composition of claim 10, wherein the phosphate backbone modification is phosphorothioate or phosphorodithioate.

12. The composition of claim 1, wherein the polynucleotide further comprises at least one modified nucleotide.

13. The composition of claim 1, wherein the antigen is a tumor antigen.

14. The composition of claim 1, wherein the antigen is a viral antigen.

15. The composition of claim 1, wherein the antigen is an allergen.

16. The composition of claim 15, wherein the allergen is Amba I.

17. The composition of claim 15, wherein the allergen is selected from the group consisting of a plant pollen allergen, an animal dander allergen, a saliva allergen, an insect allergen, and a fungal spore allergen.

18. The composition of claim 1, wherein the composition further comprises a peptide.

19. The composition of claim 18, wherein the peptide is an immunostimulatory peptide.

20. The composition of claim 1, wherein the immunomodulatory molecule further comprises a peptide.

21. The composition of claim 18 or 20, wherein the peptide is selected from the group consisting of co-stimulatory molecules, cytokines, chemokines, targeting protein ligands, and trans-activating factors.

22. The composition of claim 1, wherein the composition further comprises an adjuvant.

23. The composition of claim 1, wherein the immunomodulatory molecule further comprises an adjuvant.

24. The composition of claim 1, wherein the composition further comprises an anti-inflammatory agent.

25. The composition of claim 1, wherein the polynucleotide is linear.

26. The composition of claim 1, wherein the polynucleotide is circular.

27. The composition of claim 1, wherein the polynucleotide comprises a ribonucleotide.

28. The composition of claim 1, wherein the polynucleotide comprises a deoxyribonucleotide.

29. The composition of claim 1, wherein the antigen is covalently conjugated to the polynucleotide.

30. The composition of claim 1, wherein the antigen is non-covalently conjugated to the polynucleotide.

31. The composition of claim 1, wherein the antigen is conjugated by a linker arm to the polynucleotide.

32. A kit comprising the composition of claim 1.

33. A kit comprising the composition of claim 2.

34. A kit comprising the composition of claim 7.

35. The immunomodulatory composition of claim 22, wherein the adjuvant is not linked to the immunomodulatory molecule or the polynucleotide.

36. The immunomodulatory composition of claim 22, wherein the adjuvant is linked to the polynucleotide.

37. The immunomodulatory composition of claim 22, wherein the adjuvant is linked to the antigen.

38. The immunomodulatory composition of claim 1, wherein the ISS comprises the sequence TTCGAA.

39. The composition of claim 1, wherein the ISS is from 6 to about 200 nucleotides in length.

40. The composition of claim 1, wherein the ISS comprises the sequence 5'-TCG-3'.

41. The composition of claim 17, wherein the plant pollen allergen is a tree pollen allergen.

42. The composition of claim 1, further comprising an antibody or an antibody fragment.

43. The composition of claim 1, wherein the polynucleotide is single stranded.

44. The composition of claim 7, wherein the ISS consists of the sequence TGACTGTGAACGTTCGAGATGA (SEQ ID NO:1).

45. The composition of claim 1, wherein the ISS comprises a palindromic sequence.

46. The composition of claim 14, wherein the viral antigen is an antigen of a virus selected from a human immunodeficiency virus, a hepatitis virus, a herpes simplex virus, a rotavirus, a polio virus, a measles virus, and a human papilloma virus.

47. The composition of claim 13, wherein the composition further comprises an adjuvant.

48. The composition of claim 14, wherein the composition further comprises an adjuvant.

49. The composition of claim 15, wherein the composition further comprises an adjuvant.

50. The composition of claim 16, wherein the composition further comprises an adjuvant.

51. The composition of claim 13, wherein the antigen is covalently conjugated to the polynucleotide.

52. The composition of claim 14, wherein the antigen is covalently conjugated to the polynucleotide.

53. The composition of claim 15, wherein the antigen is covalently conjugated to the polynucleotide.

54. The composition of claim 16, wherein the antigen is covalently conjugated to the polynucleotide.

55. The composition of claim 54, wherein the ISS consists of sequence TGACTGTGAACGTTCGAGATGA (SEQ ID NO:1).

56. The composition of claim 13, wherein the ISS-PN comprises a phosphate backbone modification which is phosphorothioate.

57. The composition of claim 14, wherein the ISS-PN comprises a phosphate backbone modification which is phosphorothioate.

58. The composition of claim 15, wherein the ISS-PN comprises a phosphate backbone modification which is phosphorothioate.

59. The composition of claim 16, wherein the ISS-PN comprises a phosphate backbone modification which is phosphorothioate.

\* \* \* \* \*